United States Patent
Wennen et al.

(10) Patent No.: US 11,166,868 B2
(45) Date of Patent: Nov. 9, 2021

(54) HEAD AND NECK COMPRESSION GARMENT

(71) Applicant: TACTILE SYSTEMS TECHNOLOGY, INC., Minneapolis, MN (US)

(72) Inventors: Darren Jay Wennen, Edina, MN (US); Wade Andrew Zander, Minneapolis, MN (US); Daniel G. Chase, Menomonie, WI (US); Kristian Dior Gamble, Minneapolis, MN (US); Mark R. Riley, Minneapolis, MN (US); Alison Humble Golla, Minneapolis, MN (US); Sunday Jo Hoy, St. Paul, MN (US); Julie Louise Green, Minneapolis, MN (US); Jason Grant Tilk, Cleveland Heights, OH (US); Jason R. Ertel, Twinsburg, OH (US); Rachel Nottingham Colosimo, Cleveland Heights, OH (US); Carolyn Marie McNeeley, University Heights, OH (US); Rebecca L. Blice, Akron, OH (US)

(73) Assignee: Tactile Systems Technology, Inc., Minneapolis, MN (US)

( * ) Notice: Subject to any disclaimer, the term of this patent is extended or adjusted under 35 U.S.C. 154(b) by 685 days.

(21) Appl. No.: 15/284,888

(22) Filed: Oct. 4, 2016

(65) Prior Publication Data
US 2017/0095395 A1    Apr. 6, 2017

Related U.S. Application Data

(60) Provisional application No. 62/237,192, filed on Oct. 5, 2015, provisional application No. 62/237,200, filed
(Continued)

(51) Int. Cl.
*A61H 9/00*     (2006.01)
*A61F 13/14*    (2006.01)
(Continued)

(52) U.S. Cl.
CPC ............. *A61H 9/0078* (2013.01); *A41D 1/00* (2013.01); *A61F 5/02* (2013.01); *A61F 5/3707* (2013.01);
(Continued)

(58) Field of Classification Search
CPC ........ A61H 9/00; A61H 9/005; A61H 9/0078; A61H 2201/5002; A61H 2201/0103;
(Continued)

(56) References Cited

U.S. PATENT DOCUMENTS 1,309,783 A      7/1919  Slawin
1,608,239 A *   11/1926  Rosett .................. A61H 9/0078
                                                    128/DIG. 20
(Continued)

FOREIGN PATENT DOCUMENTS

EP    2168555 A1    3/2010
EP    2 226 044 A2  9/2010
(Continued)

OTHER PUBLICATIONS

PCT/US2016/055283, filed Oct. 4, 2016; International Preliminary Report on Patentability, dated Apr. 19, 2018; 10 pages.
(Continued)

*Primary Examiner* — Timothy A Stanis
*Assistant Examiner* — Matthew R Moon
(74) *Attorney, Agent, or Firm* — Mueting Raasch Group

(57) ABSTRACT

Compression garments and methods may include a head garment configured to be positioned around both sides of a head of a body from a posterior of the head to an anterior of the head (e.g., wherein the head garment may include a
(Continued)

plurality of controllable head pressure applying regions positionable proximate at least cheeks and a posterior of the head) and a neck garment (e.g., coupled to the head garment). The compression garments and methods may also include a torso garment. Such garment portions may include one or more controllable pressure applying regions to move lymph from the head downward.

28 Claims, 19 Drawing Sheets

Related U.S. Application Data on Oct. 5, 2015, provisional application No. 62/237,209, filed on Oct. 5, 2015.

(51) Int. Cl.
<table>
<tr><td>A61F 13/12</td><td>(2006.01)</td></tr>
<tr><td>A41D 1/00</td><td>(2018.01)</td></tr>
<tr><td>A61F 5/37</td><td>(2006.01)</td></tr>
<tr><td>A61F 5/02</td><td>(2006.01)</td></tr>
<tr><td>A41D 13/12</td><td>(2006.01)</td></tr>
</table>

(52) U.S. Cl.
CPC .............. *A61F 13/12* (2013.01); *A61F 13/14* (2013.01); *A41D 13/1245* (2013.01); *A41D 2400/322* (2013.01); *A61H 2201/0103* (2013.01); *A61H 2201/0192* (2013.01); *A61H 2201/1604* (2013.01); *A61H 2201/165* (2013.01); *A61H 2201/168* (2013.01); *A61H 2201/1609* (2013.01); *A61H 2201/1614* (2013.01); *A61H 2201/1619* (2013.01); *A61H 2201/1623* (2013.01); *A61H 2201/1645* (2013.01); *A61H 2201/1652* (2013.01); *A61H 2201/50* (2013.01); *A61H 2201/5002* (2013.01); *A61H 2201/5007* (2013.01); *A61H 2201/5071* (2013.01); *A61H 2201/5097* (2013.01); *A61H 2205/02* (2013.01); *A61H 2205/04* (2013.01); *A61H 2205/08* (2013.01)

(58) Field of Classification Search
CPC ........ A61H 2201/0192; A61H 2201/16; A61H 2201/1602; A61H 2201/1604; A61H 2201/1609; A61H 2201/1614; A61H 2201/1619; A61H 2201/1623; A61H 2201/1645; A61H 2201/165; A61H 2201/1652; A61H 2201/168; A61H 2201/50; A61H 2201/5007; A61H 2201/5071; A61H 2201/5097; A61H 2205/02; A61H 2205/022; A61H 2205/023; A61H 2205/025; A61H 2205/04; A61H 2205/08; A61F 5/02; A61F 5/3707; A61F 13/12; A61F 13/14; A41D 1/00; A41D 13/1245; A41D 2400/322
USPC .................................................. 601/148–152
See application file for complete search history.

(56) References Cited

U.S. PATENT DOCUMENTS

| | | | |
|---|---|---|---|
| 1,795,893 A | 3/1931 | Rosett | |
| D113,429 S | 2/1939 | Mehl | |
| 2,823,668 A | 2/1958 | Van Court et al. | |
| 3,094,118 A * | 6/1963 | De Geneste | A61H 9/0078 601/152 |
| 3,159,160 A | 12/1964 | Ullom | |
| 3,397,688 A | 8/1968 | Gottfried | |
| 3,606,890 A * | 9/1971 | Gilbert | A61F 7/02 607/104 |
| 3,659,593 A | 5/1972 | Vail | |
| D224,282 S | 7/1972 | Candela | |
| D253,976 S | 1/1980 | Davidson | |
| 4,210,147 A | 7/1980 | Nestor et al. | |
| 4,317,239 A | 3/1982 | Bryska | |
| D293,932 S | 1/1988 | Ramseyer | |
| 4,765,338 A | 8/1988 | Turner et al. | |
| 4,787,372 A | 11/1988 | Ramseyer | |
| 4,920,963 A * | 5/1990 | Brader | A61F 7/106 607/109 |
| 4,937,880 A | 7/1990 | Beard | |
| D311,261 S | 10/1990 | Avey | |
| 5,014,365 A | 5/1991 | Schulz | |
| 5,031,246 A | 7/1991 | Kronenberger | |
| D331,300 S | 11/1992 | Fountain | |
| 5,349,702 A | 9/1994 | Runckel | |
| 5,449,379 A | 9/1995 | Hadtke | |
| D383,204 S | 9/1997 | Lomas | |
| 5,792,082 A * | 8/1998 | Yamanaka | A61H 9/0078 601/148 |
| 5,848,982 A * | 12/1998 | Hoshino | A61H 9/0078 601/150 |
| 5,928,262 A * | 7/1999 | Harber | A61H 23/02 2/206 |
| 5,976,099 A | 11/1999 | Kellogg | |
| 5,997,465 A | 12/1999 | Savage et al. | |
| 6,030,412 A | 2/2000 | Klatz et al. | |
| 6,039,704 A * | 3/2000 | Domenighini | A61H 9/0078 601/148 |
| 6,126,683 A | 10/2000 | Momtahemi | |
| 6,179,796 B1 | 1/2001 | Waldridge | |
| 6,551,280 B1 | 4/2003 | Knighton et al. | |
| 6,592,535 B2 | 7/2003 | Ravikumar | |
| 6,645,165 B2 | 11/2003 | Waldridge et al. | |
| 6,860,862 B2 | 3/2005 | Waldridge et al. | |
| 6,966,884 B2 | 11/2005 | Waldridge et al. | |
| D522,179 S | 5/2006 | Wright | |
| 7,044,924 B1 | 5/2006 | Roth et al. | |
| D532,511 S | 11/2006 | Amarasinghe | |
| 7,396,345 B2 | 7/2008 | Knighton et al. | |
| D587,408 S | 2/2009 | Leonardi | |
| D596,805 S | 7/2009 | Leonardi | |
| 7,591,050 B2 | 9/2009 | Hammerslag | |
| D604,910 S | 11/2009 | Smaller | |
| 7,631,382 B2 | 12/2009 | Dibenedetto et al. | |
| 7,691,084 B2 | 4/2010 | Knighton et al. | |
| 7,698,909 B2 | 4/2010 | Hannula et al. | |
| 7,771,376 B2 | 8/2010 | Roth et al. | |
| D624,705 S | 9/2010 | Wright | |
| 7,857,777 B2 | 12/2010 | Larson et al. | |
| 7,887,501 B2 | 2/2011 | Riordan et al. | |
| 7,947,003 B2 | 5/2011 | Bonnefin et al. | |
| 8,046,937 B2 | 11/2011 | Beers et al. | |
| 8,096,964 B1 | 1/2012 | Bruehwiler et al. | |
| 8,226,698 B2 | 7/2012 | Edelman et al. | |
| D668,000 S | 9/2012 | Folkesson et al. | |
| 8,273,114 B2 | 9/2012 | Wasowski | |
| 8,381,362 B2 | 2/2013 | Hammerslag et al. | |
| D690,487 S | 10/2013 | Lee | |
| D692,186 S | 10/2013 | Phillips | |
| D706,990 S | 6/2014 | Martin | |
| 8,764,689 B2 | 7/2014 | Toth | |
| D729,457 S | 5/2015 | Kim | |
| 9,027,408 B2 | 5/2015 | Toth et al. | |
| D733,361 S | 6/2015 | Welborn | |
| D740,934 S | 10/2015 | Formica et al. | |
| D743,110 S | 11/2015 | Welborn | |
| D750,843 S | 3/2016 | Welborn | |
| D751,211 S | 3/2016 | Moreland | |
| D751,768 S | 3/2016 | Kim | |
| 9,320,307 B2 * | 4/2016 | Berns | A41D 13/0015 |
| D767,115 S | 9/2016 | Mingo | |
| D777,380 S | 1/2017 | Win | |
| D782,030 S | 3/2017 | Prentice et al. | |
| 9,591,884 B2 | 3/2017 | Jurga et al. | |
| D784,515 S | 4/2017 | Prentice et al. | |

(56) References Cited

U.S. PATENT DOCUMENTS

| | | |
|---|---|---|
| D797,277 S | 9/2017 | Blanch et al. |
| D810,277 S | 2/2018 | Amarasinghe et al. |
| 10,022,289 B2 * | 7/2018 | Ajiki .................... A61H 7/001 |
| D833,682 S | 11/2018 | Greenblat et al. |
| D834,179 S | 11/2018 | Smith |
| D837,971 S | 1/2019 | Prentice et al. |
| D839,484 S | 1/2019 | Chase et al. |
| 2003/0032905 A1 | 2/2003 | Waldridge et al. |
| 2003/0199922 A1 | 10/2003 | Buckman |
| 2004/0054306 A1 * | 3/2004 | Roth .................... A61H 9/0078 601/152 |
| 2005/0060789 A1 | 3/2005 | Waldman |
| 2006/0085881 A1 | 4/2006 | Gellis et al. |
| 2006/0130213 A1 | 6/2006 | Mickle |
| 2006/0156517 A1 | 7/2006 | Hammerslag et al. |
| 2007/0088234 A1 * | 4/2007 | Tseng .................... A61H 7/006 601/151 |
| 2007/0169378 A1 | 7/2007 | Sodeberg et al. |
| 2009/0178176 A1 | 7/2009 | Rowe et al. |
| 2009/0254014 A1 | 10/2009 | Son |
| 2009/0299259 A1 | 12/2009 | Cumming et al. |
| 2010/0031963 A1 | 2/2010 | Lee et al. |
| 2010/0228171 A1 | 9/2010 | Waldridge |
| 2010/0016775 A1 | 10/2010 | Cumming et al. |
| 2011/0009793 A1 | 1/2011 | Lucero et al. |
| 2011/0036358 A1 * | 2/2011 | Mattalino .......... A61F 13/00987 128/857 |
| 2011/0071447 A1 * | 3/2011 | Liu .................... A61H 9/0092 601/151 |
| 2011/0087142 A1 | 4/2011 | Ravikumar et al. |
| 2011/0087143 A1 * | 4/2011 | Bobey .................. A61H 9/0078 601/152 |
| 2011/0172579 A1 | 7/2011 | Chiu et al. |
| 2011/0185482 A1 | 8/2011 | Godfrey et al. |
| 2011/0257463 A1 | 10/2011 | Nour et al. |
| 2012/0004587 A1 | 1/2012 | Nickel et al. |
| 2012/0023648 A1 * | 2/2012 | Dainese ............... A41D 13/018 2/456 |
| 2012/0116291 A1 * | 5/2012 | Mogi .................... A61M 35/00 604/23 |
| 2012/0150086 A1 | 6/2012 | Cohen |
| 2012/0179084 A1 | 7/2012 | Lipshaw et al. |
| 2012/0296252 A1 | 11/2012 | Cumming et al. |
| 2013/0012847 A1 | 1/2013 | Lowe et al. |
| 2013/0012856 A1 | 1/2013 | Hammerslag et al. |
| 2013/0079854 A1 | 3/2013 | Wasowski |
| 2013/0152930 A1 | 6/2013 | Votel et al. |
| 2013/0269219 A1 | 10/2013 | Burns et al. |
| 2013/0345612 A1 | 12/2013 | Bannister et al. |
| 2014/0018752 A1 | 1/2014 | Shuler |
| 2014/0033402 A1 | 2/2014 | Donnadieu et al. |
| 2014/0094728 A1 | 4/2014 | Soderberg et al. |
| 2014/0123449 A1 | 5/2014 | Soderberg et al. |
| 2014/0130803 A1 | 5/2014 | Feldhahn et al. |
| 2014/0222121 A1 | 8/2014 | Spence et al. |
| 2014/0276271 A1 * | 9/2014 | Stryker .................. A61H 23/04 601/46 |
| 2015/0157484 A1 | 6/2015 | Ex-Lubeskie et al. |
| 2015/0224011 A1 * | 8/2015 | Scott .................... A61H 7/001 601/84 |
| 2015/0224012 A1 * | 8/2015 | Wright .................. A61H 9/0078 601/150 |
| 2016/0022528 A1 * | 1/2016 | Wyatt .................... A61H 7/007 601/152 |
| 2016/0058644 A1 * | 3/2016 | Cheatham, III ....... A61H 1/008 601/84 |
| 2016/0213548 A1 * | 7/2016 | John ...................... A61H 1/02 |
| 2016/0220808 A1 * | 8/2016 | Hyde .................... A61N 1/0452 |
| 2017/0105893 A1 * | 4/2017 | Kim, II .................. A61H 39/04 |

FOREIGN PATENT DOCUMENTS

| | | |
|---|---|---|
| EP | 2 462 905 B1 | 11/2013 |
| EP | 2671560 A1 | 12/2013 |
| FR | 2 624 003 A1 | 11/1988 |
| FR | 2 93 9 642 A1 | 6/2010 |
| GB | 699152 | 10/1953 |
| WO | WO 03/041621 A1 | 5/2003 |
| WO | WO 2008/033963 A2 | 3/2008 |
| WO | WO 2014/159706 A2 | 10/2014 |
| WO | WO 2015/200203 A1 | 12/2015 |
| WO | WO 2015/2002031 A1 | 12/2015 |

OTHER PUBLICATIONS

U.S. Appl. No. 29/576,157, filed Aug. 31, 2016, Chase et al.
U.S. Appl. No. 29/576,182, filed Aug. 31, 2016, Chase et al.
U.S. Appl. No. 15/284,858, filed Oct. 4, 2016, Wennen et al.
U.S. Appl. No. 15/284,870, filed Oct. 4, 2016, Wennen et al.
U.S. Appl. No. 15/286,378, filed Oct. 5, 2016, Chase et al.
U.S. Appl. No. 15/319,179, filed Dec. 15, 2016, Chase et al.
U.S. Appl. No. 15/411,003, filed Jan. 20, 2017, Wennen et al.
U.S. Appl. No. 15/411,059, filed Jan. 20, 2017, Chase et al.
U.S. Appl. No. 29/595,538, filed Feb. 28, 2017, Chase et al.
U.S. Appl. No. 29/596,757, filed Mar. 10, 2017, Wennen et al.
[European Patent Office] International Patent Application No. PCT/US2016/055283, filed Oct. 4, 2016; [International Search Report / Written Opinion] dated Dec. 20, 2016; 15 pages.

* cited by examiner

HEAD AND NECK COMPRESSION GARMENT

CROSS-REFERENCE TO RELATED APPLICATIONS

This application claims the benefit of U.S. Provisional Application No. 62/237,209, filed Oct. 5, 2015, and entitled "Head and Neck Compression Garment"; U.S. Provisional Application No. 62/237,200, filed Oct. 5, 2015, and entitled "Static and Dynamic Compression Therapy System"; and U.S. Provisional Application No. 62/237,192, filed Oct. 5, 2015, and entitled "Head and Neck Compression Therapy System," both of which are incorporated herein in their entirety.

FIELD OF THE DISCLOSURE

The present disclosure relates generally to the use of compression garments and compression garment systems and to methods for applying pressure to a portion of the body (e.g., a portion of a head and a neck of a body).

BACKGROUND

Various types of compression garments are available, for example, such as for treatment of lymphedema, edema, wound healing, etc. For example, garments may include inflatable cells (or other actuatable elements) to provide therapy to patients and may be positioned about any body portion of a person or animal. Specifically, the garments may be positioned about body portions that exhibit swelling due to a build-up of lymph and that would benefit from compression therapy provided by the garments. For example, such cells may be inflatable to one or more different pressures in a variety of sequences to provide the therapy to the patient by moving lymph from one region to another. In other words, such compression garments may be placed around at least a portion of an individual's body for use in applying pressure to the body at an affected extremity. These compression garments may be donned (e.g., put on) and doffed (e.g., taken off) by patients themselves or with help from others.

SUMMARY

An exemplary compression garment described herein may include a head garment including a plurality of head pressure applying regions controllable to apply pressure to one or more portions of a head of a body, a torso garment including a plurality of torso pressure applying regions controllable to apply pressure to one or more portions of a torso of the body, and a neck garment locatable between at least a portion of the head garment and at least a portion of the torso garment (e.g., the neck garment may be coupled between a portion of the head garment and a portion of the torso garment, or the neck garment may just be coupled to a portion of the head garment). The head garment may include a posterior head garment portion, a right head garment portion, and a left head garment portion. The posterior head garment portion may be positionable proximate a posterior of the head of the body. The right head garment portion may extend from the posterior head garment portion and may be positionable to wrap around a right side of the head from the posterior of the head to an anterior of the head. The left garment portion may extend from the posterior head garment portion opposite the right head garment portion and may be positionable to wrap around a left side of the head from the posterior of the head to the anterior of the head. The torso garment may include a posterior torso garment portion, a right torso garment portion, and a left torso garment portion. The posterior torso garment portion may be positionable proximate a posterior of the torso of the body. The right torso garment portion may extend from the posterior torso garment portion and may be positionable to an anterior of the torso. The left torso garment portion may extend from the posterior torso garment portion opposite the right torso garment portion and may be positionable to the anterior of the torso. The plurality of head and torso pressure applying regions may be controllable to move lymph from the head downward to the torso of the body.

In one or more embodiments, the neck garment may include at least one pressure applying region controllable to apply pressure to a portion of the neck to at least move lymph from the head downward towards the torso of the body. In one or more embodiments, each of the plurality of head and torso pressure applying regions may be controllable to apply pressure to move lymph at least from the left and right sides of the head towards the posterior of the head and from the posterior of the head downward towards the torso. In one or more embodiments, the compression garment may be controllable by a controller configured to control each of the plurality of head and torso pressure applying regions to move lymph at least from the head towards the torso.

In one or more embodiments, the right torso garment portion may be positionable proximate a right anterior portion and a right side of the torso and the left torso garment portion may be positionable proximate a left anterior portion and a left side of the torso. At least one of the plurality of torso pressure applying regions may be controllable to apply pressure to the right and left anterior portions of the torso and the right and left sides of the torso. In one or more embodiments, the right torso garment portion may define a right arm opening proximate a right arm of the body and the left torso garment portion may define a left arm opening proximate a left arm of the body. In one or more embodiments, the right torso garment portion and the left torso garment portion may overlap proximate the anterior of the torso when positioned on the body.

In one or more embodiments, the neck garment portion may include a right neck garment portion positionable around a right side of the neck from a posterior of the neck to an anterior of the neck and a left neck garment portion positionable around a left side of the neck from a posterior of the neck to an anterior of the neck. The right neck garment portion may include pressure applying regions separate from pressure applying regions of the left neck garment portion. In one or more embodiments, the compression garment may be controllable by a controller configured to control pressure applied by the right and left neck garment portions alternately.

In one or more embodiments, the garment further may include fastening apparatus configured to couple the right torso garment portion to the left torso garment portion proximate the anterior of the torso. The fastening apparatus may include a right strap couplable to the right torso garment portion, a left strap couplable to the left torso garment portion, and a fastener configured to couple the right strap to the left strap. In one or more embodiments, the left and right straps may be couplable on the left and right torso garment portions, respectively, using hook and loop fasteners.

In one or more embodiments, each of the plurality of head and torso pressure applying regions may include one or more cells configured to receive a fluid (e.g., air). In one or more embodiments, the plurality of head pressure applying regions may include one or more actuatable elements configured to apply pressure to the one or more portions of the head and the plurality of torso pressure applying regions may include one or more actuatable elements configured to apply pressure to the one or more portions of the torso. In one or more embodiments, the neck garment may define a neck open region proximate an anterior portion of the neck of the body adjacent the trachea when positioned on the body. In one or more embodiments, the head garment may define one or more head open regions proximate a top portion of the head.

In one or more embodiments, the right head garment portion may be positionable proximate a right cheek of the head of the body and the left head garment may be positionable proximate a left cheek of the head of the body. Each of the plurality of head pressure applying regions may be controllable to apply pressure to a portion of right and left cheeks. In one or more embodiments, the head garment may include an under chin garment portion positionable proximate under a chin of the head and the under chin garment portion may be configurable to apply pressure to a portion under the chin. In one or more embodiments, the under chin garment portion may include one or more under chin pressure applying regions controllable to apply pressure to a portion under the chin. In one or more embodiments, the under chin garment portion may include one or more under chin connection elements configured for use in donning the head garment on the head of the body. The one or more under chin connection elements may be configured to connect the right head garment portion and the left head garment portion.

In one or more embodiments, the head garment may include a forehead garment portion positionable proximate a forehead of the head. The forehead garment portion may include one or more forehead connection elements configured for use in donning the head garment on the head. In one or more embodiments, the forehead garment portion may be configurable to apply pressure to a portion of the forehead. In one or more embodiments, the head garment may include one or more nasal connection elements positionable proximate a nasal bridge of the head. The one or more nasal connection elements may be configured to connect the right head garment portion and the left head garment portion.

An exemplary method of donning a compression garment on at least a portion of a body described herein may include donning a torso garment on a torso of the body and donning a head garment on the body. The torso garment may include a plurality of torso pressure applying regions controllable to apply pressure to one or more portions of a torso of the body. The head garment may be coupled to the torso garment by a neck garment (or the head garment may be separate from the torso garment) and may include a plurality of head pressure applying regions controllable to apply pressure to one or more portions of a head of the body. Donning the torso garment may include positioning a posterior torso garment portion of the torso garment proximate a posterior of the torso of the body. Donning the torso garment may also include positioning a right torso garment portion of the torso garment (e.g., extending from the posterior torso garment portion) to an anterior of the torso and positioning a left torso garment portion of the torso garment (e.g., extending from the posterior torso garment portion opposite the right torso garment portion) to the anterior of the torso. Donning the torso garment may further include coupling the left and right torso garment portions. Donning the head garment may include positioning a posterior head garment portion of the head garment proximate a posterior of the head of the body. The donning the head garment may also include positioning a right head garment portion of the head garment (e.g., extending from the posterior head garment portion) around a right side of the head from the posterior of the head to an anterior of the head and positioning a left head garment portion of the head garment (e.g., extending from the posterior head garment portion opposite the right head garment portion) around a left side of the head from the posterior of the head to the anterior of the head. Donning the head garment may further include coupling the right and left head garment portions.

In one or more embodiments, the coupling of the left and right torso garment portions may include coupling the left and right torso garment portions using fastening apparatus. In one or more embodiments, the head garment may include an under chin garment portion positionable proximate under a chin of the head. The under chin garment portion may be configurable to apply pressure to a portion under the chin. In one or more embodiments, the under chin garment portion may include one or more under chin connection elements configured for use in coupling the right and left head garment portions. In one or more embodiments, the head garment may include a forehead garment portion positionable proximate a forehead of the head. The forehead garment portion may be configured for use in coupling the right and left head garment portions. In one or more embodiments, the head garment may include one or more nasal connection elements positionable proximate a nasal bridge of the head. The one or more nasal connection elements may be configured for use in coupling the right and left head garments.

In one or more embodiments, each of the plurality of head and torso pressure applying regions may be controllable to apply pressure to a portion of the body to move lymph at least from the left and right sides of the head towards the posterior of the head and from the posterior of the head downward towards the torso. In one or more embodiments, the neck garment may include at least one pressure applying region controllable to apply pressure to a portion of the neck to move lymph from the head downward towards the torso of the body. In one or more embodiments, the method may also include applying pressure to the head of the body by at least one of the plurality of head pressure applying regions and applying pressure to the torso of the body by at least one of the plurality of torso pressure applying regions. In one or more embodiments, the method may further include repeating applying pressure to the head of the body and applying pressure to the torso of the body.

An exemplary compression garment described herein may include a head garment configured to be positioned around both sides of a head of a body from a posterior of the head to an anterior of the head and a neck garment coupled to the head garment and configured to be positioned around both sides of a neck of the body from a posterior of the neck to an anterior of the neck. The head garment may include a plurality of controllable head pressure applying regions positionable proximate at least cheeks and a posterior of the head. The neck garment may include at least one controllable neck pressure applying regions.

In one or more embodiments, the compression garment may be controllable by a controller configured to control each of the plurality of head controllable pressure applying regions to apply pressure to the cheeks and the posterior of the head and each of the at least one neck controllable pressure applying regions to apply pressure to a portion of the neck to move lymph at least from the cheeks towards the neck and downwards. In one or more embodiments, each of the plurality of controllable head pressure applying regions and each of the at least one controllable neck pressure applying regions may include one or more cells configured to receive a fluid (e.g., air). In one or more embodiments, each of the plurality of controllable head pressure applying regions may include one or more head actuatable elements configured to apply pressure to the cheeks and posterior of the head and each of the at least one controllable neck pressure applying regions may include one or more neck actuatable elements configured to apply pressure to the portion of the neck. In one or more embodiments, the neck garment portion may define an open region proximate an anterior portion of the neck of the body adjacent the trachea when positioned on the body.

In one or more embodiments, the neck garment portion may include a right neck garment portion positionable proximate a right portion of the neck of the body and a left neck garment portion positionable proximate a left portion of the neck of the body. The right neck garment portion may include pressure applying regions separate from pressure applying regions of the left neck garment portion. In one or more embodiments, the compression garment may be controllable by a controller configured to control pressure applied by the right and left neck garment portions alternately. In one or more embodiments, the compression garment system may also include a torso garment coupled to the neck garment and configured to be positioned around both sides of a torso of the body from a posterior of the torso to an anterior of the torso. The torso garment may include a plurality of controllable torso pressure applying regions.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1A:
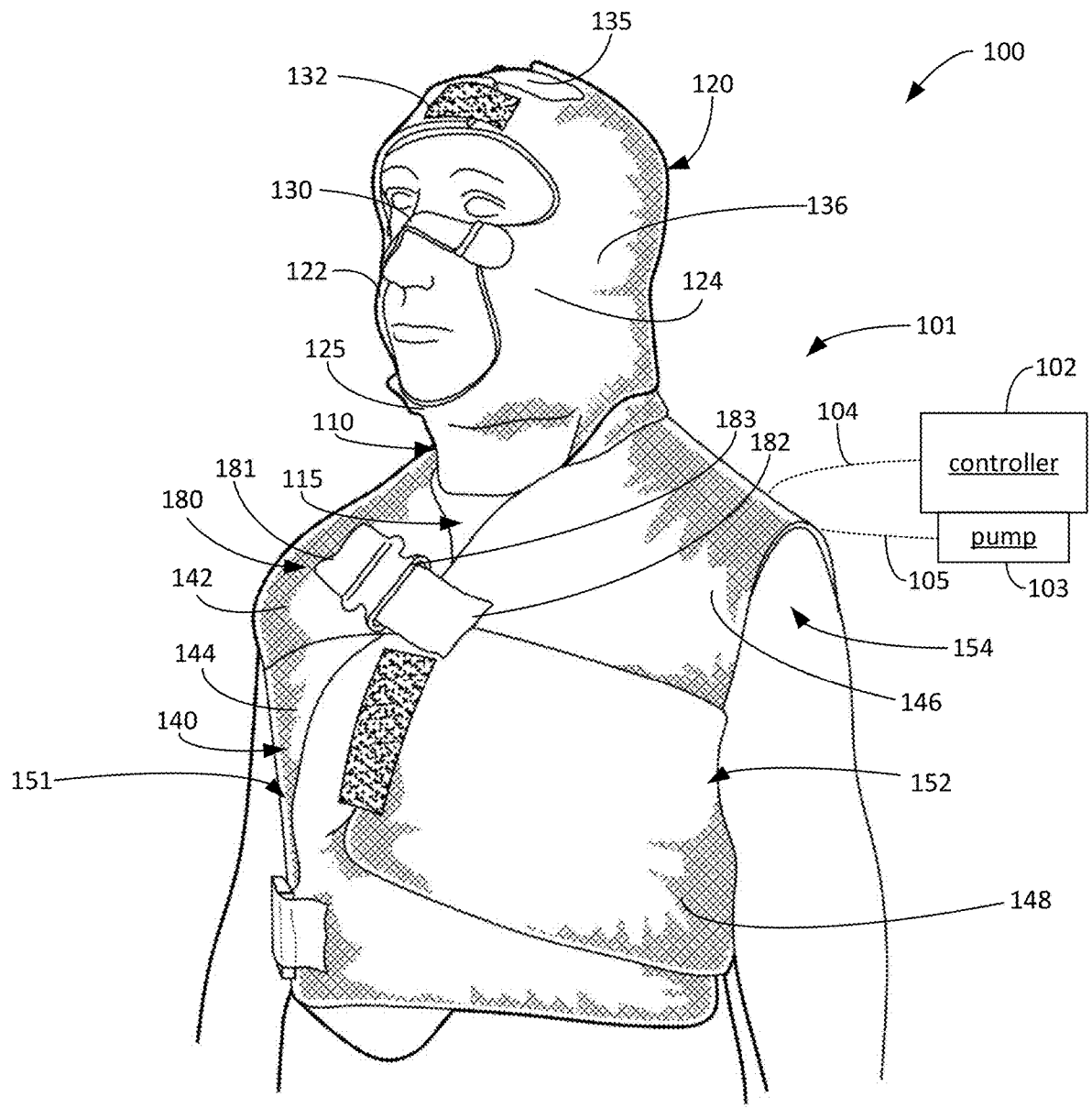
FIG. 1A is a front perspective view of an exemplary compression system located on a body.

In the following detailed description of illustrative embodiments, reference is made to the accompanying figures of the drawing, which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary apparatus, systems, structures, and methods shall be described with reference to FIGS. 1-14. It will be apparent to one skilled in the art that elements from one embodiment may be used in combination with elements of the other embodiments, and that the possible embodiments of such apparatus and systems using combinations of features set forth herein is not limited to the specific embodiments shown in the Figures and/or described herein. Further, it will be recognized that the embodiments described herein may include many elements that are not necessarily shown to scale. Still further, it will be recognized that the size and shape of various elements herein may be modified but still fall within the scope of the present disclosure, although certain one or more shapes and/or sizes, or types of elements, may be advantageous over others.

The present disclosure relates generally to compression garments that include garment portions that are configured to be donned on at least a portion of a body (e.g., person, animal, etc.) and configured to apply pressure to that portion of the body, compression garment systems that include compression garments and apparatus for controlling pressure applied to at least a portion of a body, and methods using such compression garments and compression garment systems (e.g., methods of donning a garment, methods of controlling pressure applied to the body, methods of applying a static and/or dynamic pressure, etc.)

Compression garment systems (e.g., such as compression garments described in U.S. Pat. No. 6,179,796 entitled "Lymphedema treatment system," U.S. Pat. No. 6,645,165 entitled "Lymphedema treatment system," U.S. Pat. No. 6,860,862 entitled "Lymphedema Treatment System," and U.S. Pat. No. 6,966,884 entitled "Lymphedema Treatment System," which are herein incorporated by reference and which may modify and be modified with features described herein) may be used for various reasons including therapy for people with lymphedema, animals requiring therapy, wound therapy, etc. As used herein, the term body refers to not only humans but any other animal species that may benefit from the concepts and features described herein. These compression garments may be placed around at least a portion of an individual's body and used to apply pressure to the body at an affected extremity (e.g., head, neck, arm, torso, a shoulder, etc.). Some embodiments described herein may include a compression system having a garment configured to be positioned on (e.g., wrapped around, placed adjacent, located in proximity to, etc.) at least a portion of a body (e.g., human body, arm, torso, a shoulder, head, neck, etc.). The compression garments may be donned (e.g., put on) and doffed (e.g., taken off) by individuals themselves or with help from others. The garment may also include one or more cells (e.g., compartments) distributed along a length of the garment configured to receive a fluid (e.g., air) to perform compression therapy.

The compression therapy provided by the compression garment systems may help to treat lymphedema. Lymphedema is a condition of localized fluid retention and tissue swelling that may be inherited, caused by cancer treatments, caused by parasitic infections, etc. For example, lymphedema of the head and neck may cause swelling around the head, neck, submandibular area, cheek, nose, eyelids, etc. Compression garments described herein covering the head and neck may be used by an affected individual to provide a therapeutic benefit. Specifically, the compression garments may be configured to manipulate lymph nodes or vessels by applying pressure to move lymph toward more beneficial locations (e.g., toward drainage areas, away from affected regions, etc.). For example, compression therapy using the systems described herein may be performed around the head and neck area to help treat lymphedema in the head and neck area by, e.g., moving lymph towards the torso.

The compression garments described herein may be configured to apply pressure to the affected regions of the body to apply compression therapy. The compression garments may include various portions that each includes controllable pressure applying regions. Each controllable pressure applying region may be configured to apply pressure to a specific portion of the body (e.g., at a specific time during therapy). The controllable pressure applying regions may work in combination with one another to help provide therapy by applying a sequence of pressures on the body that moves lymph in a desired direction (e.g., from the head towards the neck, from the neck towards the torso, etc.). Such application of a sequence of pressures on the body that moves lymph (e.g., pressure being applied to one or more portions of the head and neck, at different times during a compression therapy period) may be referred to as applying dynamic pressure to the body.

The controllable pressure applying regions of the compression garments may also apply static pressure to the body. For example, the compression garments may apply a constant pressure when a portion of the garment is positioned on the body over a therapy time period (e.g., static pressure over the therapy time period) or may apply a pressure that may be controlled to change over time during the therapy time period (e.g., dynamic pressure). In one or more embodiments, the dynamic pressure may be applied to the portion of the body through one or more cells in the compression garment. The one or more cells may be configured to receive fluid. Alternately, or in combination with one or more fluid receiving cells, such pressures may be applied using one or more actuatable elements in the compression garment configured to apply pressure to the body (e.g., electrically controlled materials suitable to provide compression).

Figure 1B:
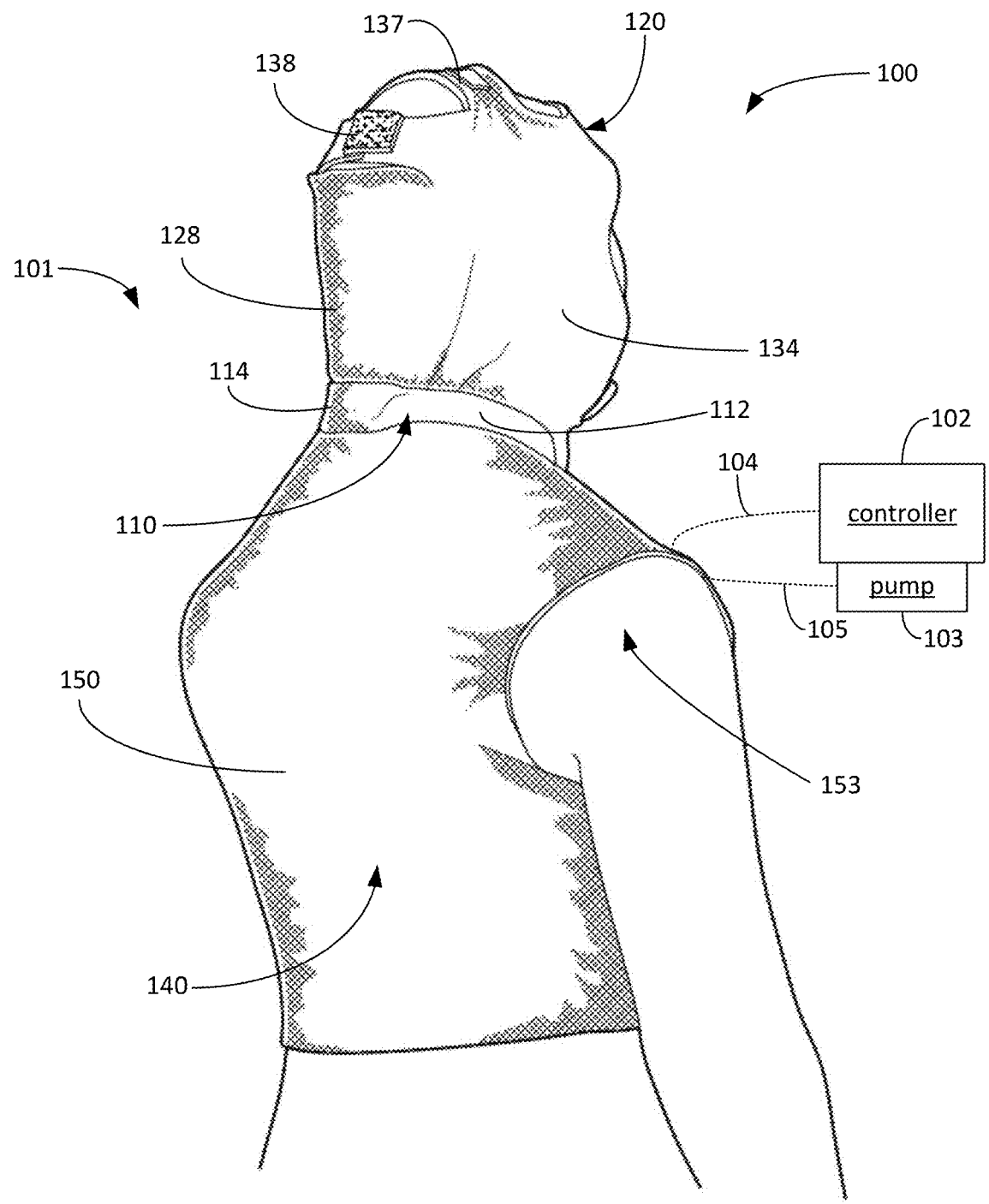
FIG. 1B is a rear perspective view of the exemplary compression system of FIG. 1A located on the body.
Figure 2A:
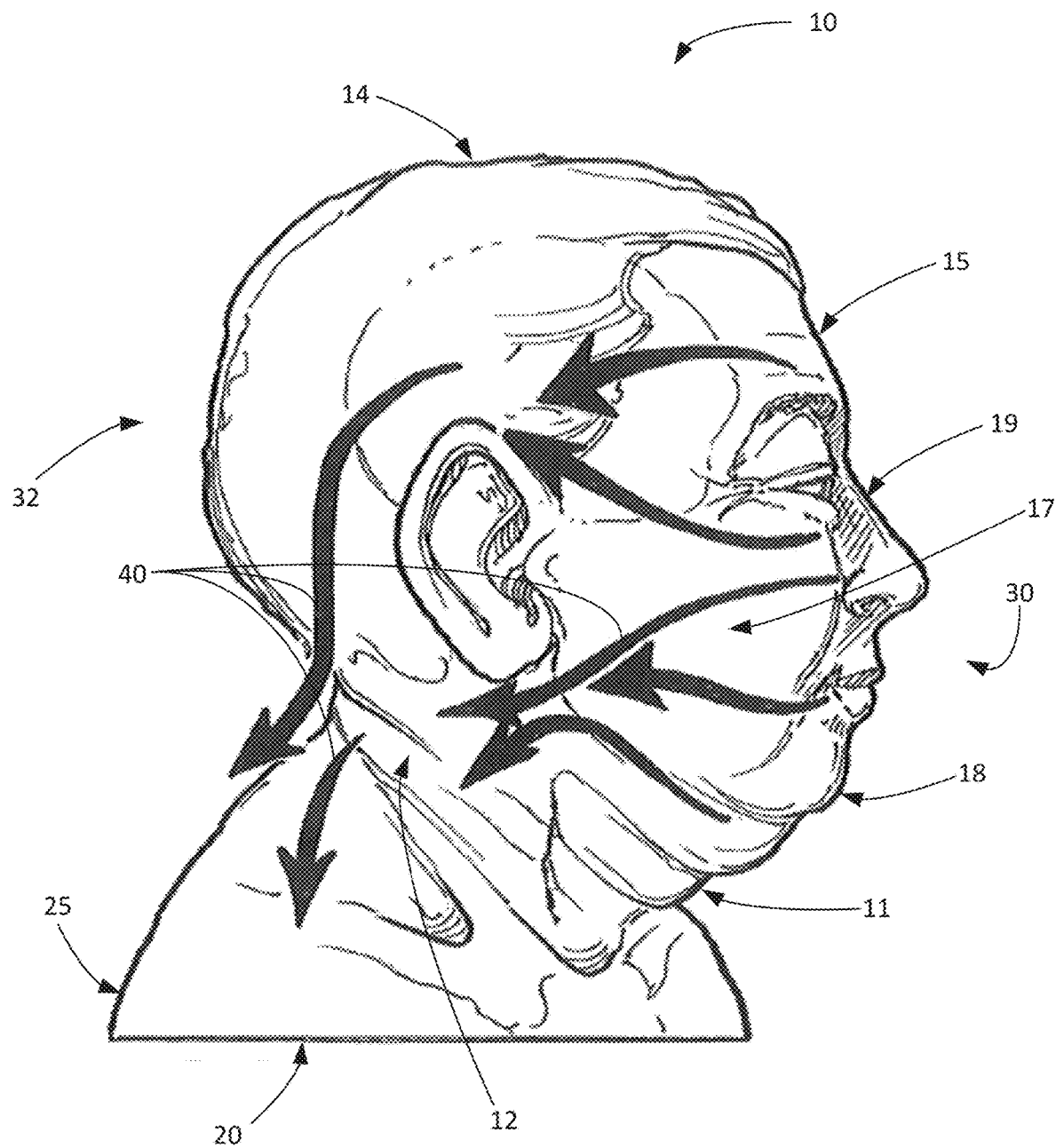
FIG. 2A is an exemplary side view of a head and a neck of a human body illustrating the directional flow of lymph through the head and neck using the exemplary compression system.
Figure 2B:
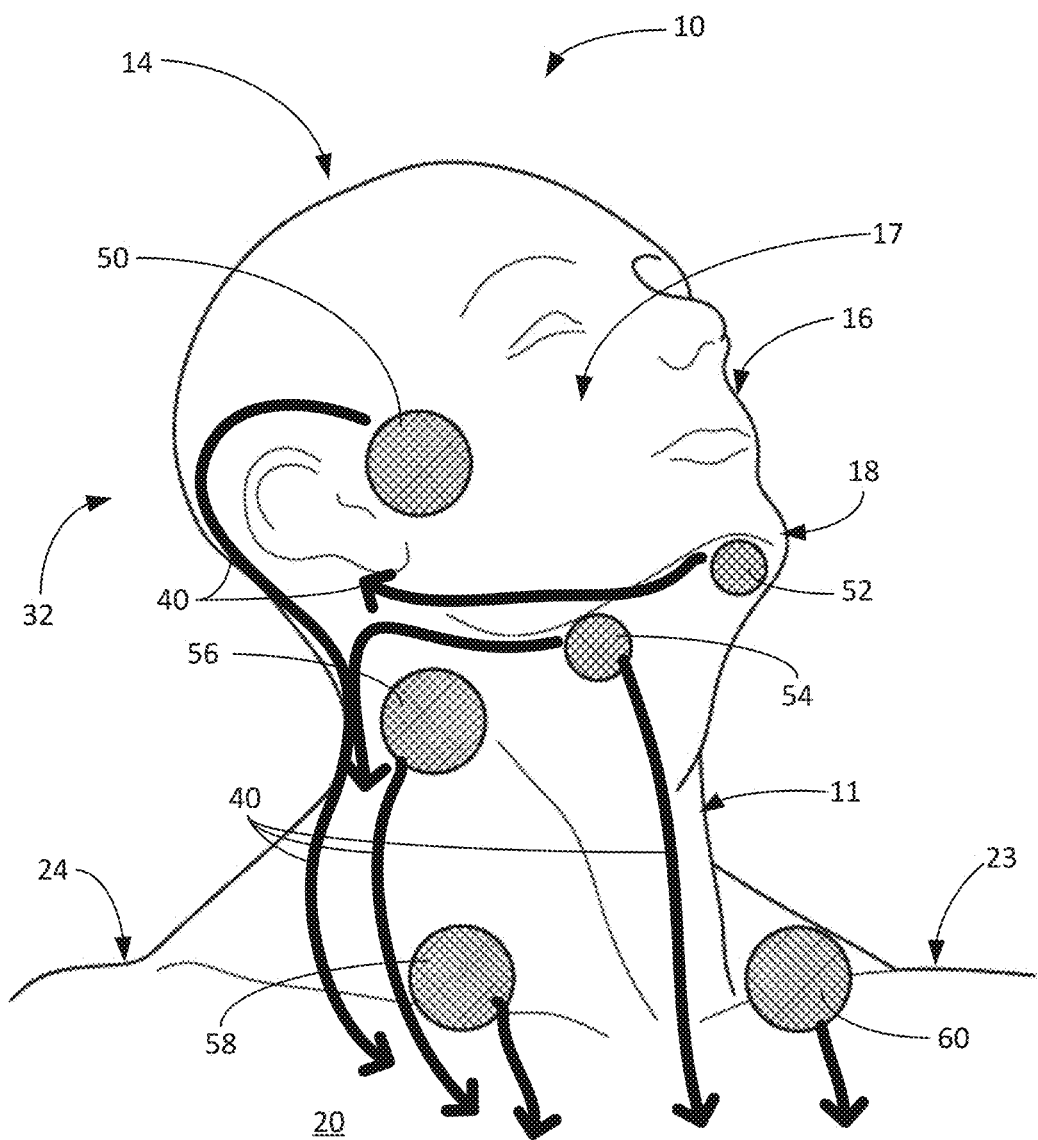
FIG. 2B is a perspective view of a head and a neck of a human body illustrating specific lymph nodes and the directional flow of lymph through the head and neck using the exemplary compression system.
Figure 2C:
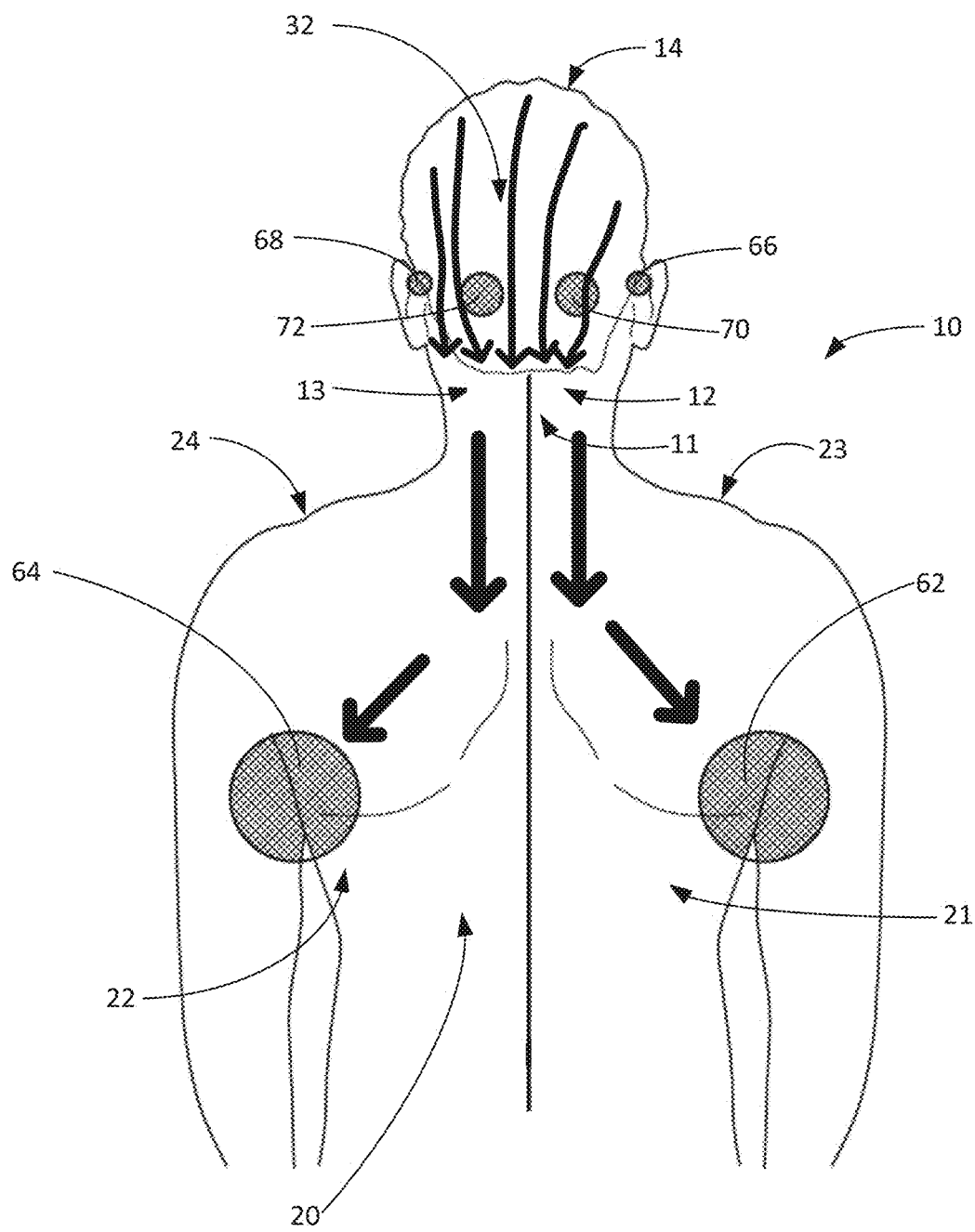
FIG. 2C is an exemplary back view of a human body illustrating specific lymph nodes and the directional flow of lymph through the body using the exemplary compression system.

An exemplary compression garment system 100 including a garment 101 (e.g., compression garment) configured to be positioned around at least a portion of a body (e.g., a human body 10 as shown in FIGS. 2A-2C) is shown in FIGS. 1A-1B. The garment 101 may be positioned relative to the body in a variety of different ways (e.g., relative to a head 14, a neck 11, an anterior portion of the body 10, a posterior portion of the body 10, a forehead 15, under a chin 18, a left and right cheek 16, 17, a torso 20 as shown in FIGS. 2A-2C). For example, as shown in FIGS. 1A-1B the garment 101 is positioned around the head, neck and torso of the body. In one or more embodiments, the garment 101 may also cover the arms, waist, legs, or any other portion of the body.

As shown in FIGS. 1A-1B the garment 101 is positioned on the head, neck and torso of the body. In other embodiments, the garment 101 may include only portions positioned on the head and neck of the body. Still further, in other embodiments, the garment 101 may include only portions positioned on the head of the body. The garment 101 may include a head garment portion 120 positioned proximate the head and a neck garment portion 110 positioned proximate the neck.

In one or more embodiments, the head garment portion 120 and the neck garment portion 110 may be coupled to one another. For example, the head garment portion 120 and the neck garment portion 110 may be coupled to one another at the posterior of the body, the anterior of the body, along the portion in which the head and neck garment portions 120, 110 intersect, etc. Still further, in one or more embodiments, the head garment portion 120 and the neck garment portion 110 may be coupled to one another along the entire portion in which the head and neck garment portions 120, 110 intersect (e.g., where such portions lie next to one another) or only along portions thereof (e.g., leaving openings at the coupling region for the garment to flex and adapt to the body of the user).

The garment 101 may also include a torso garment portion 140 configured to be positioned proximate the torso of the body. In one or more embodiments, the torso garment portion 140 may be couplable to the neck garment portion 110 (e.g., the torso garment portion 140 may be separate from the head garment or the head and neck garment, may be removably couplable to the head garment or the head and neck garment, for example, using hook and loop fasteners, etc.). For example, torso garment portion 140 and the neck garment portion 110 may be coupled to one another at the posterior of the body, the anterior of the body, along the portion in which the torso garment portion 140 and neck garment portion 110 intersect, etc. Still further, in one or more embodiments, the torso garment portion 140 and the neck garment portion 110 may be coupled to one another along the entire portion in which the torso garment portion 140 and neck garment portions 110 intersect (e.g., where such portions lie next to one another) or only along portions thereof (e.g., leaving openings at the coupling region for the garment to flex and adapt to the body of the user).

As shown in FIGS. 1A-1B, the garment 101 may also include an open region 115 between the neck garment portion 110 and the torso garment portion 140 proximate the anterior portion of the neck and adjacent the trachea when the garment 101 is positioned on the body. The open region 115 may allow access to the airway of an individual wearing the garment 101.

The garment 101 may include pressure applying regions (e.g., as shown in FIGS. 3-7) located at regions of the garment 101. Each of the pressure applying regions may be controllable or configurable to apply pressure to a portion of the body. For example, the head garment portion 120 may include head pressure applying regions that are controllable or configurable to apply pressure to one or more portions of the head (e.g., to the forehead, cheeks, under the chin, posterior head), the neck garment portion 110 may include neck pressure applying regions that are controllable or configurable to apply pressure to one or more portions of the neck (e.g., posterior neck regions, side neck regions, etc.), and the torso garment portion 140 may include torso pressure applying regions controllable or configurable to apply pressure to one or more portions of the torso (e.g., torso regions under each arm, the anterior torso, the posterior torso, etc.). As shown in FIGS. 1A-1B, the garment 101 may include an exterior material covering the pressure applying regions.

The head garment portion 120 may be configured to be donned on the head of the body. In other words, the head garment portion 120 may be positioned on and secured to the head of the body (e.g., secured using fasteners across the nose, fasteners across the forehead, fasteners under the chin, fasteners over the top of the head, etc.). For example, such fastening apparatus may allow one garment to be adjusted for use with different size and shaped body parts. In one or more embodiments, the head garment portion 120 may be described as configured to be positioned around both sides of the head of the body from the posterior of the head to the anterior of the head.

The head garment portion 120 may include a posterior head garment portion 128, a right head garment portion 134, and a left head garment portion 136. The posterior head garment portion 128 may be positionable proximate a posterior of the head of the body. The right head garment portion 134 may extend from the posterior head garment portion 128 and be positionable on (e.g., wrapped around) a right side of the head from the posterior of the head to an anterior of the head. The left head garment portion 136 may extend from the posterior head garment portion 128 and be positionable on (e.g., wrapped around) a left side of the head from the posterior of the head to the anterior of the head. The posterior head garment portion 128, the right head garment portion 134, and the left head garment portion 136 (or each of such portions) may include pressure applying regions (e.g., each of the one or more head pressure applying regions for applying compression on regions of the body associated with each of such portions, one or more head pressure applying regions for applying compression on one or more regions of the body corresponding to one or more portions of the garment, etc.) that are configurable or controllable to apply pressure to the posterior of the head, the right side of the head, and the left side of the head.

The head garment portion 120 may also include a right cheek garment portion 122 and a left cheek garment portion 124. The right cheek garment portion 122 may be positionable proximate a right cheek of the head and the left cheek garment portion 124 may be positionable proximate a left cheek of the head. Each of the right and left cheek garment portions 122, 124 may include pressure applying regions (e.g., one or more cheek pressure applying regions) that may be configurable or controllable to apply pressure to a portion of cheek. The head garment portion 120 may also include an under chin garment portion 125. The under chin garment portion 125 may include pressure applying regions (e.g., one or more under chin pressure applying regions) that may be configurable to apply pressure to a portion under the chin (e.g., at the "waddle" area).

The head garment portion 120 may be donned on the head of the body in a variety of different ways. For example, portions of the head garment portion 120 may be attached to other portions of the head garment portion 120 using a variety of different straps or connection elements. Any suitable connection apparatus may be used for donning the head garment portion 120 or any other garment portion described herein, such as flexible or rigid connection elements, hook and loop fasteners, straps connected to the garment, additional or separate connection garment elements or straps, mating hooks, elements shaped to form to a body part (such as the bridge of the nose), etc.

These straps and connection elements may keep portions of the head garment portion 120 (e.g., surfaces associated with pressure applying regions) close to the surface of body such that the head garment portion 120 may effectively apply pressure to a particular portion of the body (e.g., the cheeks, under the chin, forehead, temples), such as, for example, when fluid is provided to cells of pressure applying regions. In other words, the straps or connection elements may assist in preventing the head garment portion 120 from moving away from the surface of portion of the body when pressure is being applied using pressure applying regions (e.g., such as when fluid is provided to cells of pressure applying regions) and instead, e.g., stay near the portion of the body such that pressure may be effectively applied. The different straps or connection elements keep the garment portions from moving away from the body as pressure is being applied such that even pressure applying regions (e.g., to apply pressure evenly) at edges of the garment are maintained in position during application of pressure to body regions adjacent such edges (e.g., garment edges proximate the cheeks of the head, garment edges near the chin of the head, garment edges near under the chin, garment edges near the temples of the head, etc.).

For example, the head garment portion 120 may include the under chin garment portion 125, one or more nasal connection elements 130, a forehead garment portion 132, a top head strap 137, and a posterior head strap 138, each of which may act as straps or connection elements to keep the head garment portion 120 in place. The under chin garment portion 125 may include one or more under chin connection elements 127 configured to connect the right cheek garment portion 122 and the left cheek garment portion 124. The one or more under chin connection elements 127 may also be configured for use in donning the head garment portion 120 on the head of the body (e.g., tightening the head garment portion 120 into place on the head). In other words, the one or more under chin connection elements 127 may pull the right and left cheek garment portions 122, 124 closer to one another when the head garment portion 120 is positioned on the head to assist in donning the head garment portion 120 on the head.

The one or more nasal connection elements 130 may be positionable proximate a nasal bridge of the head and configured to connect the right cheek garment portion 122 and the left cheek garment portion 124 to, e.g., maintain the head garment portion 120 and right and left cheek garment portions 122, 124 proximate the surface of the head and cheeks. For example, the one or more nasal connection elements 130 may include a rigid portion shaped to be positioned adjacent the surface of the nasal bridge of the head (e.g., which rigid portion may be connected to the right cheek garment portion 122 and the left cheek garment portion 124 by one or more flexible portions).

The forehead garment portion 132 may be positionable proximate a forehead of the head. The forehead garment portion 132 may include one or more forehead connection elements that may be configured for use in donning the head garment portion 120 on the head. In other words, the one or more forehead connection elements may pull one portion of the head garment portion 120 closer to another portion of the head garment portion 120 to position (e.g., secure) the head garment portion 120 on the head of the body. In one or more embodiments, the head garment portion 120 may include one or more straps positioned proximate the top of the head and configured to assist in donning the head garment portion 120 on the head. For example, the top head strap 137 and the posterior head strap 138 may be positioned proximate the top of the head and the posterior of the head, respectively, and may assist in donning the head garment portion 120 to the head. In one or more embodiments, the top head strap 137 and the posterior head strap 138 may cover the entire top of the head. As shown in FIGS. 1A-1B, the head garment portion 120 defines a head open region 135 proximate a top portion of the head and, e.g., between the top head strap 137 and the posterior head strap 138.

One will recognize that any number of straps or connection elements may be used to connect different portions of the head garment such that the pressure applying regions thereof are properly positioned adjacent desired regions of the head and maintained in positioned as pressure is being applied either dynamically or statically.

The neck garment portion 110 coupled to the head garment portion 120 is shown in FIGS. 1A-1B. The neck garment portion 110 may be configured to be donned on a neck of the body. In one or more embodiments, the neck garment portion 110 may be described as configured to be positioned around both sides of the neck from the posterior of the neck to the anterior of the neck. The neck garment portion 110 may include pressure applying regions (e.g., one or more neck pressure applying regions) that may be configurable or controllable to apply pressure to a portion of the neck.

The neck garment portion 110 may include a first neck garment portion (e.g., right neck garment portion 112) and a second neck garment portion (e.g., left neck garment portion 114). The first neck garment portion may be positionable proximate a right portion or side of the neck and the second neck garment portion may be positionable proximate a left portion or side of the neck. In one or more embodiments, the first neck garment portion (e.g., right neck garment portion 112) may be described as being positionable on (e.g., wrapped around) a right side of the neck from a posterior of the neck to an anterior of the neck and the second neck garment portion (e.g., left neck garment portion 114) may be described as being positionable on (e.g., wrapped around) a left side of the neck from the posterior of the neck to the anterior of the neck.

In one or more embodiments, the first neck garment portion is separate from the second neck garment portion (e.g., one portion may include pressure applying regions separate from those in the other portion). In other embodiments, the first and second garment portions may be one piece. Each of the first and second neck garment portions may be configurable or controllable to apply pressure to the right and left sides of the neck, respectively. For example, the pressure applying regions of first and second neck garment portions may be controllable or configurable to apply pressure alternately between each of the first and second neck garment portions, or simultaneously. Specifically, the pressure applying regions of first and second neck garment portions may be controllable or configurable to apply pressure alternately during a therapy cycle of a therapy period (e.g., first neck garment portion then second neck garment portion then first neck garment portion and so on) between each of the first and second neck garment portions to help minimize the chances of an individual passing out as lymph passes from the head through the neck to the torso during compression therapy.

The garment 101 may also include a torso garment portion 140 positionable proximate a torso of the body as shown in FIGS. 1A-1B. In one or more embodiments, the torso garment portion 140 may be described as configured to be positioned around both sides of the torso from the posterior of the torso to the anterior of the torso. The torso garment portion 140 may include pressure applying regions (e.g., one or more torso pressure applying regions) configurable or controllable to apply pressure to one or more portions of the torso. In one or more embodiments, the torso garment portion 140 may be coupled to the head garment portion 120. Further, in one or more embodiments, the neck garment portion 110 may be coupled between at least a portion of the head garment portion 120 and at least a portion of the torso garment portion 140. In yet other embodiments, the torso garment portion 140 may not be coupled to either the head garment portion 120 or the neck garment portion 110. Further, the torso garment portion 140 may include a collar portion locatable proximate the neck of the body (e.g., usable to cover the neck of the body with or without the neck garment portion, for example, removably couplable to the neck garment portion, overlapping with the neck garment portion when donned, etc.).

The torso garment portion 140 may include a posterior torso garment portion 150, a right torso garment portion 151, and a left torso garment portion 152. The posterior torso garment portion 150 may be positionable proximate a posterior of the torso of the body, the right torso garment portion 151 may extend from the posterior torso garment portion 150 and be positionable to the anterior of the torso, and the left torso garment portion 152 may extend from the posterior torso garment portion 150 and be positionable to the anterior of the torso. In one or more embodiments, the right torso garment portion 151 and the left torso garment portion 152 may overlap proximate the anterior of the torso when the garment 101 is positioned on the body (e.g., as shown in FIG. 1A, at least a portion of the left torso garment portion 152 overlaps a portion of the right torso garment portion 151). In one or more embodiments, the right torso garment portion 151 may define a right arm opening 153 proximate a right arm of the body such that the right arm may extend outward from the garment 101 and the left torso garment portion 152 may define a left arm opening 154 proximate a left arm of the body such that the left arm may extend outward from the garment 101.

The right and left torso garment portions 151, 152 may be coupled to each other after donning the torso garment portion 140 on the torso of the body to attach (e.g., secure) the torso garment portion 140 to the torso. The right torso garment portion 151 may be coupled to the left torso garment portion 152 in any suitable manner. For example, the right and/or left torso garment portions 151, 152 may include fastening apparatus to, e.g., fasten or couple a region of the right torso garment portion 151 to a region of the left torso garment portion 152. Such fastening apparatus may include hook and loop fasteners, or any other fasteners described herein.

Further, for example, the garment 101 may include fastening apparatus 180 (e.g., fastening structures) configured to couple the right torso garment portion 151 to the left torso garment portion 152 (e.g., proximate the anterior of the torso). For example, the fastening apparatus 180 may include a right strap 181 couplable to the right torso garment portion 151, a left strap 182 couplable to the left torso garment portion 152, and a fastener 183 configured to couple the right strap 181 to the left strap 182. The fastener 183 may include a right clasp coupled to the right strap 181 and a left clasp coupled to the left strap 182. The right clasp may engage the left clasp to secure the fastener 183. The right and left straps 181, 182 may be couplable on the right and left torso garment portions 151, 152, respectively, using hook and loop fasteners. In other words, the right and left straps 181, 182 may be adjustable on the right and left torso garment portions 151, 152 and then coupled together using the fastener 183 (e.g., such as user releasable mating elements, etc.). This allows the right and left straps 181, 182 to be placed on the torso garment portion 140 in an initial fitting of the torso garment portion 140 on a patient, but then the torso garment portion 140 may be donned and doffed with more ease using the fastener 183. For example, it provides the torso garment portion 140 to be easily released and re-engaged by the individual wearing the torso garment portion 140.

In one or more embodiments, the fastening apparatus 180 may include a right fastening portion that is removably couplable to the torso garment portion 140 (e.g., at the right torso garment portion 151) and a left fastening portion that is removably couplable to the torso garment portion 140 (e.g., at the left torso garment portion 152). The right and left fastening portions may be coupled to the torso garment portion 140 using, e.g., hook and loop fasteners or any other suitable fastener. The right and left fastening portions may be coupled together using a zipper or any other suitable way to couple the portions together. This design allows the right and left fastening portions to be placed initially to fit the torso garment portion 140 and then the torso garment portion 140 may be donned and doffed (e.g., tightened and loosened) through zipping and unzipping the zipper. In other words, the right and left fastening portions may stay attached to the torso garment portion 140 and only the zipper would need to move to don and doff the torso garment portion 140.

The right torso garment portion 151 may include a right chest garment portion 142 and a right axillary garment portion 144. Each of the right chest garment portion 142 and the right axillary garment portion 144 may extend from the posterior torso garment portion 150 to the anterior of the torso. The right chest garment portion 142 may extend from a right shoulder of the torso towards a right anterior region of the torso (e.g., right side of chest, right side of lower abdomen). The right axillary garment portion 144 may be positionable proximate a right under arm region of the torso.

The left torso garment portion 152 may include a left chest garment portion 146 and a left axillary garment portion 148. Each of the left chest garment portion 146 and the left axillary garment portion 148 may extend from the posterior torso garment portion 150 to the anterior of the torso. The left chest garment portion 146 may extend from a left shoulder of the torso towards a left anterior region of the torso (e.g., left side of chest, left side of lower abdomen). The left axillary garment portion 148 may be positionable proximate a left under arm region of the torso.

The compression garment system 100 may also include a controller 102 or control apparatus configured to control the pressure applied to the portion of the body by each of the pressure applying regions of the garment 101. For example, the controller 102 may control the pressure applied to the portion of the body by each of the pressure applying regions independent from one another or at the same time. Further, for example, the pressure applying regions may be controlled in groups or combinations. In one or more embodiments, the controller 102 may be configured to control the pressure applying regions in a variety of different sequences (e.g., applying pressure in a predetermined manner) that may be, e.g., suitable for carrying out lymphedema therapy.

Further, the controller 102 may control the pressure based on one or more pressures measured by one or more pressure sensors associated with the garment 101 (e.g., sensors provided in the garment 101 proximate the pressure applying regions). One or more compression garments that may be modified with features (e.g., sensors) described herein may be similar to and include one or more features found in U.S. Pat. No. 6,860,862 entitled "Lymphedema Treatment System," U.S. Pat. No. 6,966,884 entitled "Lymphedema Treatment System," U.S. Pat. No. 6,179,796 entitled "Lymphedema treatment system," and U.S. Pat. No. 6,645,165 entitled "Lymphedema treatment system," which are herein incorporated by reference.

In one or more embodiments, a control apparatus or controller 102 (e.g., one or more processors employing one or more programs or routines carrying out one or more methods or processes and implemented with one or more types of memory) may be configured to control the system and/or one or more elements thereof (e.g., providing compression therapy by the one or more pressure applying regions, etc.). In one or more embodiments, the control apparatus may be configured to control the compression system using wired and/or wireless technology.

The methods and/or logic and/or configurations described in this disclosure, including those attributed to the systems, or various constituent components, may be implemented, at least in part, in hardware, software, firmware, or any combination thereof. For example, various aspects of the techniques may be implemented within one or more processors, including one or more microprocessors, microcontrollers, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices (e.g., within the system, outside of the system, or a combination of both) to support the various operations and functions described in this disclosure. In addition, any of the described components may be implemented together or separately as discrete but interoperable logic devices. Description of different features is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

Figure 8A:
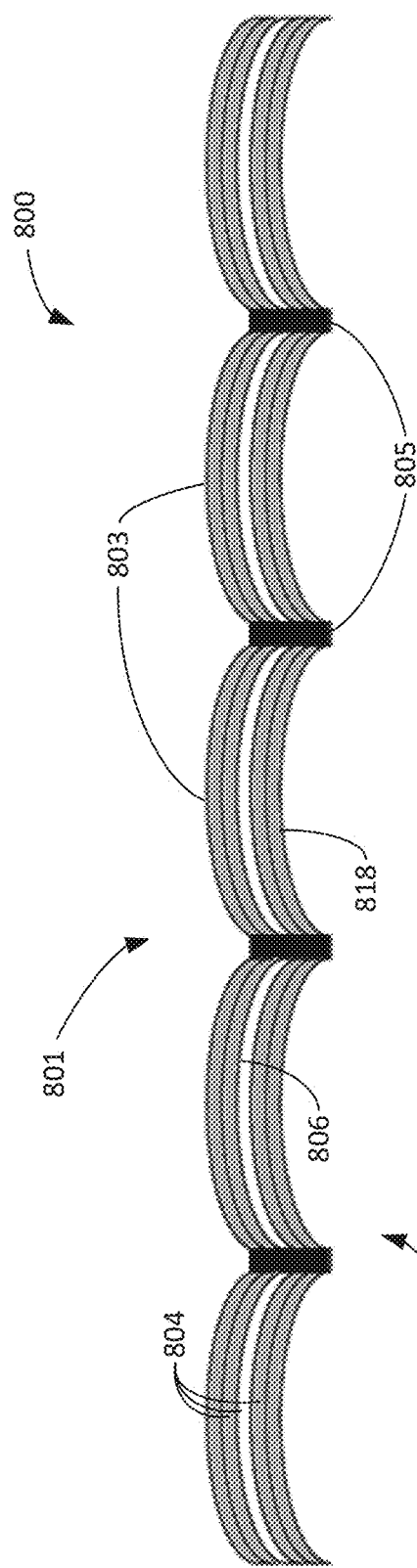
FIG. 8A is a cross-sectional view of one or more cells (e.g., inflatable cells) of an exemplary compression garment that may be used with one of the exemplary garment portions such as shown in FIGS. 1A-1B, 3-7, and 9-10.

Further, the compression garment system 100 may include a pump 103 that may be controlled by the controller 102 to provide a fluid to/from the one or more cells (e.g. one or more cells 803 as shown in FIG. 8A) of each of the pressure applying regions, e.g., a fluid such as a liquid or gas in the cells, so as to apply a compression therapy when the compression garment 101 includes one or more fluid filled cells. For example, the pump 103 may be connected to one or more of the plurality of cells corresponding to the plurality of pressure applying regions by a plurality of lines or tubing 105 so as to provide flow of fluid thereto or removal of fluid therefrom.

Further, in one or more embodiments, as shown in FIGS. 1A-1B, the controller 102 may be connected to one or more components of the compression garment system via one or more electrical lines and/or wirelessly, as represented generally by dashed lines 104. For example, controller 102 may be connected to communicate and control the pressure applying regions (e.g., such as electrically actuatable pressure applying regions of the garment configured to apply pressure to the body) either with use of physical electrical connections and/or wirelessly.

The controllable pressure applying regions of the garment 101 under control of controller 102 allows the system 100 to provide compression therapy to an individual (e.g., a patient) wearing the garment 101 such that lymph flows throughout the body 10 in desired directions, e.g., such as directions 40 as shown in FIG. 2A. In other words, by controlling the pressure applying regions in a variety of different sequences (e.g., applying pressure in a predetermined manner), for example, lymph may flow generally from the head 14 of the body 10 towards the neck 11 of the body 10. For example, the lymph may be controlled to flow from an anterior 30 of the head 14 towards a posterior 32 of the head 14 and downwards towards the neck 11. Specifically, for example, the lymph may flow from the forehead 15, the nasal bridge 19, and under the chin 18 towards the right cheek 17 and downwards towards the neck 11 (e.g., right side of neck 12) and the posterior 25 of the torso 20. This direction 40 of lymph may provide relief to an individual by moving excess lymph from the head 14, and ultimately, moving such lymph towards the torso 20 (e.g., trunk, shoulders, chest, back, waist, etc.).

The various nodes located in the head 14 and neck 11 of the body 10 are shown in FIG. 2B. For example, the submental lymph nodes 52 are located the under chin 18 of the head 14 and the parotid lymph nodes 50 are located proximate the right cheek 17 and the left cheek 16 (parotid lymph nodes of left cheek 16 not shown in FIG. 2B). The accumulation of lymph may occur near the parotid lymph nodes 50 and the submental lymph nodes 52 and may be pushed during compression therapy by the compression garment donned on the body 10 towards the posterior 32 of the head 14 as illustrated by directional arrows 40 (e.g., by controlling the pressure applying regions proximate at least the cheeks 16, 17 and under the chin 18 in a predetermined manner). With continued compression therapy (e.g., by controlling the pressure applying regions proximate at least the sides of the head 14 and the posterior 32 of the head 14), the lymph then moves towards the submandibular lymph nodes 54 and superficial and deep cervical lymph nodes 56 located proximate the neck 11. The compression therapy is then configured (e.g., by controlling the pressure applying regions proximate at least the neck 11 in a predetermined manner) to move lymph towards the right infra and supra clavicular lymph nodes 58 and the left infra and supra clavicular lymph nodes 60, which are located at the base of the neck 11 and proximate the right shoulder 24 and the left shoulder 23, respectively, and downwards towards the torso 20.

Various nodes located in the posterior 32 of the head 14 and the torso 20 are shown in FIG. 2C. During compression therapy using a compression garment (e.g., by controlling the pressure applying regions of the head garment 120 and neck garment 110 in a predetermined manner), lymph may travel downward along the posterior 32 of the body 10 from the head 14 towards the torso 20. For example, lymph may travel from the top of the head 14 towards the right retroauricular lymph nodes 66 and the right occipital lymph nodes 70 located proximate the right side 12 of the neck 11 and towards the left retroauricular lymph nodes 68 and the left occipital lymph nodes 72 located proximate the left side 13 of the neck 11. The compression therapy (e.g., by controlling the pressure applying regions of the garment 101 in a predetermined manner) may then move the lymph further downwards from the head 14 and past the right and left shoulders 23, 24 and towards the torso 20. Specifically, the lymph may move towards the right axillary nodes 62 located proximate the right under arm region 21 and the left axillary nodes 64 located proximate the left under arm region 22.

Figure 3:
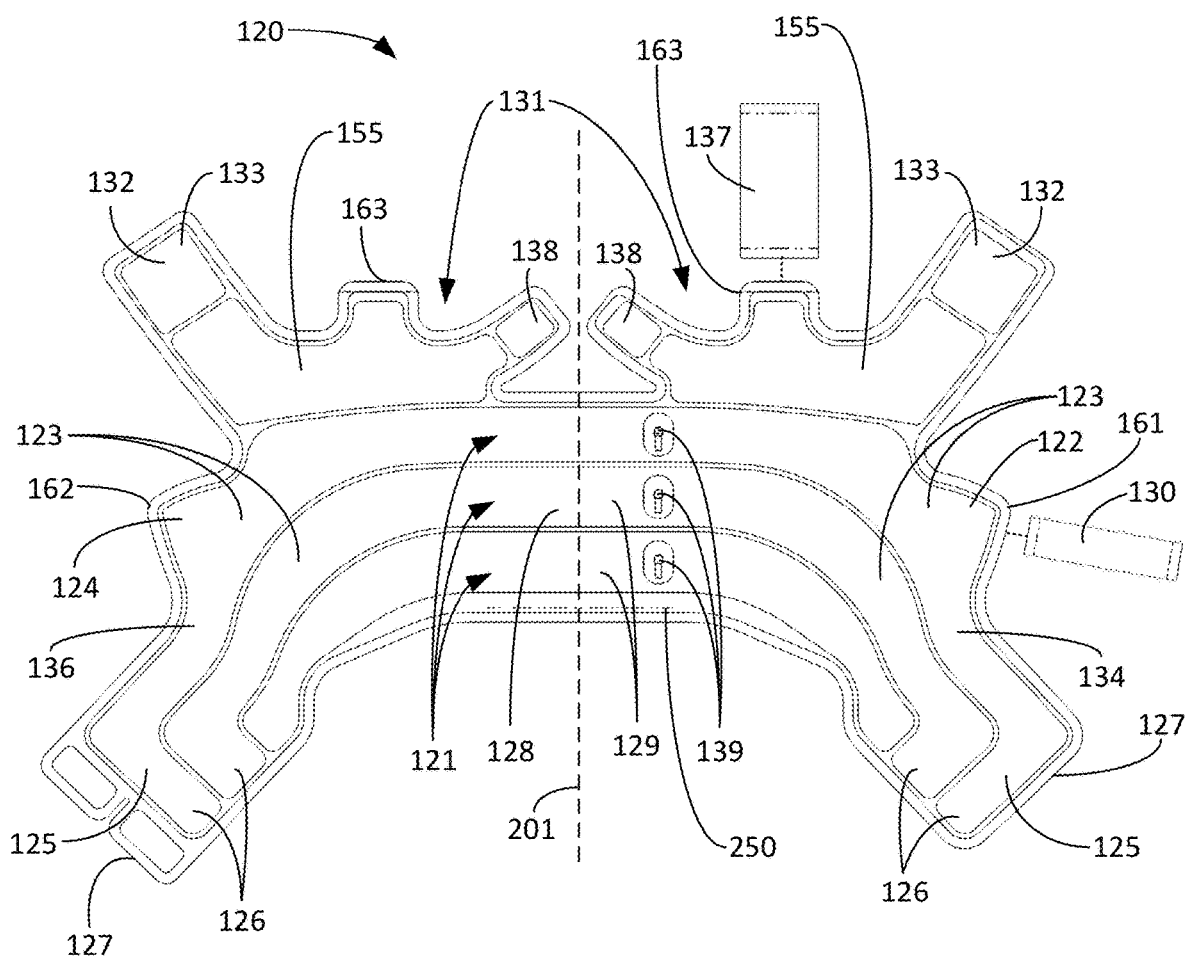
FIG. 3 is a plan view of an exemplary head garment portion of a compression garment system such as shown in FIGS. 1A-1B including one or more pressure applying regions.

A plan view of the exemplary head garment portion 120 including one or more head pressure applying regions 121 is shown in FIG. 3. In one or more embodiments, at least a portion of the one or more head pressure applying regions 121 may define an arcuate shape. The one or more head pressure applying regions 121 may be controllable (e.g., using controller 102 as shown in FIGS. 1A-1B) to apply pressure to a portion of the head when the head garment portion 120 is positioned on the head. The one or more head pressure applying regions 121 may be located in various locations within the head garment portion 120 to apply pressure to a variety of different locations on the head. For example, as described herein, the head garment portion 120 may include the right head garment portion 134 positionable proximate a right side of the head and the left head garment portion 136 positionable proximate a left side of the head. The one or more head pressure applying regions 121 associated with the right and left head garment portions 134, 136 may be controllable to apply pressure to the right and left sides of the head, respectively.

In one or more embodiments, each of the one or more head pressure applying regions 121 may be configured in any suitable manner such that the regions 121 may be controlled to apply pressure to a portion of the head. For example, the one or more head pressure applying regions 121 may include fluid chambers or cells, pneumatic pressure applying regions, actuatable elements applying pressure to regions, hydraulic pressure applying regions, etc. Specifically, the one or more head pressure applying regions 121 shown in FIGS. 3-7, as well as the other pressure applying regions of the other garment portions shown therein include one or more cells configured to receive fluid (e.g., air, liquid, etc.).

In one or more embodiments, the one or more head pressure applying regions 121 may be configured to apply pressure to a portion of the head using the one or more cells through the control of fluid provided thereto, e.g., fluid flow, air flow, etc. For example, the head garment portion 120 may include one or more head garment ports 139 through which fluid may be provided to the one or more cells (e.g., such as with use of pump 103 shown in FIGS. 1A-1B, under control of controller 102 with use of a sensor feedback system). Further, in one or more embodiments, the one or more head pressure applying regions 121 may include one or more head actuatable elements (e.g., non-fluid receiving regions) configured to apply pressure to a portion of the head (e.g., an electrical signal may be used to actuate an element within the garment, such as electrically actuatable fibers in the garment, such that the region including such fibers applies a pressure to a portion of the body). In one or more embodiments, the one or more head pressure applying regions 121 may include both one or more cells configured to receive fluid and one or more head actuatable elements, both of which may be configured to apply pressure to a portion of the head.

Furthermore, as described herein, the head garment portion 120 may include a right cheek garment portion 122 and a left cheek garment portion 124, each of which may include one or more cheek pressure applying regions 123 (e.g., each of the garment portions may include a portion of a pressure applying region shared with other garment portions, for example, the same pressure applying region may be used to apply compression at locations of the body associated with the right cheek and left cheek, and even the posterior garment portion). Each of the one or more cheek pressure applying regions 123 may be controllable to apply pressure to a portion of cheek to assist in moving lymph therefrom. Each of the right cheek garment portion 122 and the left cheek garment portion 124 may extend within the right and left head garment portions 134, 136, respectively and terminate along right cheek and left cheek garment edges 161, 162 (e.g., portions of such edges being located near the nasal bridge of the head; which portions may be coupled together by one or more nasal connection elements 130).

Similarly, as described herein, the head garment portion 120 may include the under chin garment portion 125 that is configurable to apply pressure to a portion under the chin (e.g., a "waddle" area). For example, the under chin garment portion 125 may include one or more under chin pressure applying regions 126. Each of the one or more under chin pressure applying regions 126 may be controllable to apply pressure to a portion under the chin to assist in moving lymph therefrom.

Also, as described herein, the head garment portion 120 may include the posterior head garment portion 128. The posterior head garment portion 128 may include one or more posterior head pressure applying regions 129. Each of the one or more posterior head pressure applying regions 129 may be controllable to apply pressure to a portion of the posterior of the head to move lymph therefrom (e.g., downward toward the torso).

Any number of pressure applying regions 121 may be configured in the head garment portion 120 such that they may be controlled to move lymph as described, for example, with reference to FIGS. 2A-2C. For example, as shown in FIG. 3, three head pressure applying regions 121 are implemented. However, any number of head pressure applying regions 121 may be implemented (e.g., four head pressure applying regions 121 may be used). Each of the three pressure applying regions 121 may extend along the entire length of the head garment portion 120 positionable about the head of a user (e.g., from the front right side of the head around the posterior of the head and towards the front left side of the head). For example, each of the head pressure applying regions 121 may extend within the under chin garment portion 125, the right and left cheek garment portions 122, 124, and the posterior head garment portion 128 (e.g., which may be beneficial in application of pressure in a downward and rearward manner on the head). In other words, the under chin garment portion 125, the right and left cheek garment portions 122, 124, and the posterior head garment portion 128 may be integral with each other such that head pressure applying regions 121 may span across one or more specific portions. For example, application of pressure in the outer head pressure applying region 121 (e.g., next to edges 161, 162), followed by application of pressure by more inward lying pressure applying regions, may produce desired lymph movement.

In one or more embodiments, the head pressure applying regions 121 may be positioned such that pressure may be applied in a progression from the front of the right and left cheeks (e.g., at the anterior of the head) towards the posterior of the head. For example, pressure may be applied to a region proximate the right and left cheek garment portions 122, 124 at the anterior of the head, then proximate a middle of the cheeks at the right and left cheek garment portions 122, 124, and then proximate a portion of the cheeks closer to the posterior of the head at the right and left cheek garment portions 122, 124. In one or more embodiments, as pressure is being applied at the right and left cheek garment portions 122, 124 from the anterior of the head towards the posterior of the head, pressure may also be applied at the posterior head garment portion 128 from the top of the head towards the neck. In one or more embodiments, this may occur due to the continuation of the three head pressure applying regions 121 (e.g., as shown in FIG. 3) extending (e.g., along the length of the garment) between the right and left cheek garment portions 122, 124 and across the posterior head garment portion 128 (e.g., each of such pressure applying regions may be separate cells supplied by separate fluid conduits). As described herein, when a garment portion is described as including one or more pressure applying regions, such one or more pressure applying regions may be a separate pressure applying region or may be a pressure applying regions shared with one or more other garment portions (e.g., check garment portions and posterior head garment portions may use the same pressure applying region to apply compression to a body portion associated therewith).

However, such head pressure applying regions 121 may include any number of different and separate cells along the wrappable length of the head garment portion 120 and controllable to produce such desired lymph movement. For example, the head pressure applying regions 121 may be separable between the right and left cheek garment portions 122, 124 and the posterior head garment portion 128. In other words, the head pressure applying regions 121 may be separated in any suitable way that may allow pressure to be applied from the right and left cheeks (e.g., proximate the anterior of the head) towards the posterior of the head and/or from the top of the posterior of the head towards the neck (e.g., to move lymph from the cheeks towards the neck at the posterior of the head). For example, the head pressure applying regions 121 may be separated such that each head pressure applying region 121 may be independently controllable to move lymph in a desired direction (e.g., as shown in FIGS. 2A-2C).

The head garment portion 120 may also include upper head garment portions 131 proximate the top of the head to assist in applying pressure and assist in donning the head garment portion 120. For example, the upper head garment portions 131 may include garment regions 155 adjacent the outermost pressure applying region of the three pressure applying regions 121 to assist in securing the pressure applying regions adjacent the surface of the head when pressure is being applied. Further, for example, the head garment portion 120 may include the posterior head strap 138 positionable proximate the top and posterior of the head (e.g., using hook and loop fastener connection elements), the top head strap 137 positionable proximate the top of the head (e.g., a separate strap connectable to two different regions 163 of the head garment portion 120 across the top of the head when the head garment portion 120 is donned), and the forehead garment portion 132 positionable proximate the forehead (e.g., using hook and loop fastener connection elements).

The forehead garment portion 132 may be configurable to apply pressure to a portion of the forehead. In one or more embodiments, the forehead garment portion 132 may include one or more forehead pressure applying regions 133 controllable to apply pressure to a portion of the forehead. One will recognize that any number of upper head garment portions 131 may be used to secure the head garment portion 120 on the head. For example, although the figures provided herein show straps for use in donning the head garment portion 120, the head garment portion 120 may be provided in a stocking cap like configuration where no straps are used in the entire top of the head is covered.

Figure 4:
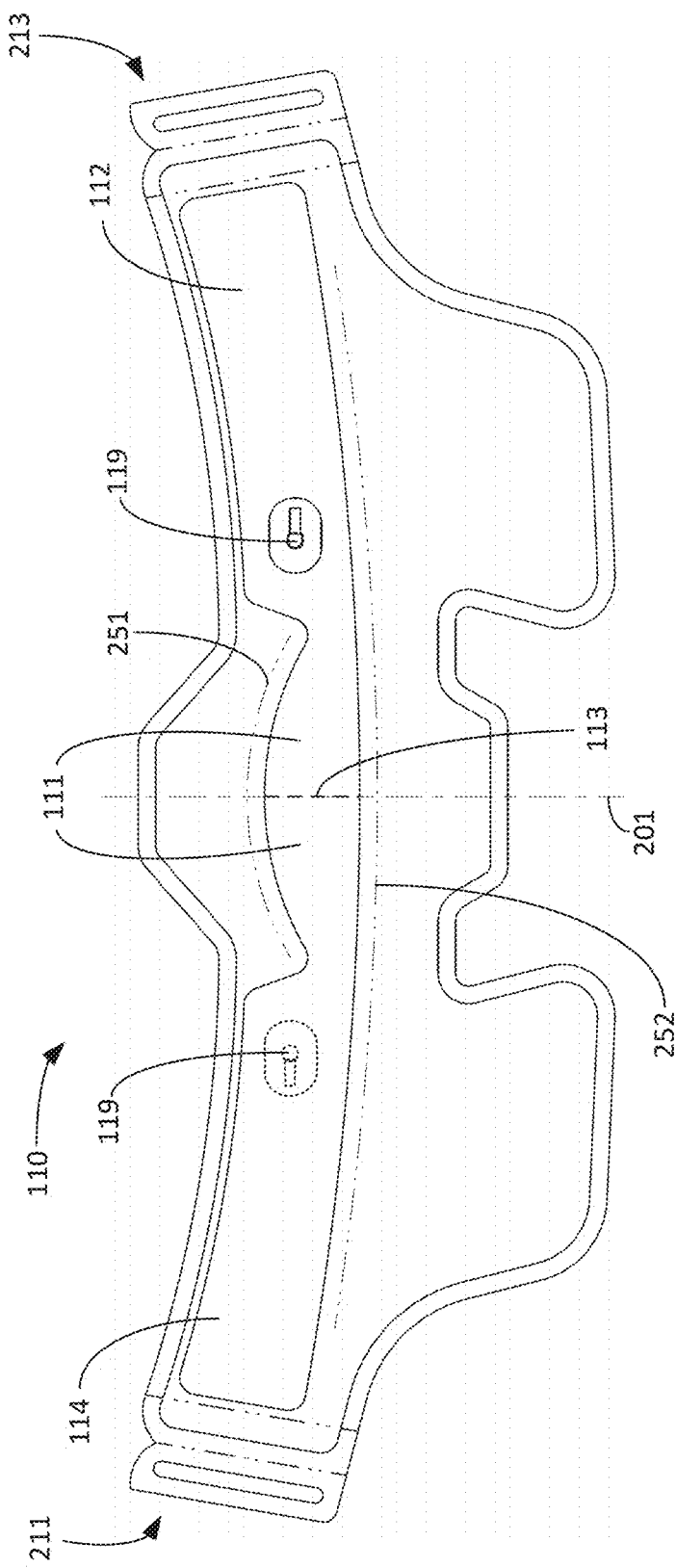
FIG. 4 is a plan view of an exemplary neck garment portion of a compression garment system such as shown in FIGS. 1A-1B including one or more pressure applying regions.

A plan view of the exemplary neck garment portion 110 including one or more neck pressure applying regions 111 is shown in FIG. 4. In one or more embodiments, at least a portion of the one or more neck pressure applying regions 111 may define an arcuate shape. The one or more neck pressure applying regions 111 may be controllable (e.g., using controller 102 as shown in FIGS. 1A-1B) to apply pressure to a portion of the neck when the neck garment portion 110 is positioned on the neck.

In one or more embodiments, the neck garment portion 110 may include a first neck garment portion (e.g., right neck garment portion 112) and a second neck garment portion (e.g., left neck garment portion 114). Each of the first and second neck garment portions may include one or more neck pressure applying regions 111. In one or more embodiments, the one or more neck pressure applying regions 111 of the first and second neck garment portions may be separated by a divider 113. In other words, the divider 113 separates pressure applied by the one or more neck pressure applying regions 111 of the first neck garment portion 112 from the one or more neck pressure applying regions 111 of the second neck garment portion 114.

In one or more embodiments, each of the one or more neck pressure applying regions 111 may be configured such that they may be controlled to apply pressure to a portion of the neck. For example, the one or more neck pressure applying regions 111 may include fluid chambers or cells, pneumatic pressure applying regions, actuatable elements applying pressure to regions, hydraulic pressure applying regions, etc. Specifically, the one or more neck pressure applying regions 111 may include one or more cells configured to receive fluid as shown in FIG. 4.

For example, in one or more embodiments, the one or more neck pressure applying regions 111 may be configured to apply pressure to a portion of the head using the one or more cells through the control of fluid provided thereto, e.g., fluid flow, air flow, etc. (e.g., such as with use of pump 103 shown in FIGS. 1A-1B, under control of controller 102 with use of a sensor feedback system). For example, the neck garment portion 110 may include one or more neck garment ports 119 through which fluid may be provided to the one or more cells. In one or more embodiments, the neck garment portion 110 may include two neck garment ports 119, one in each of the right and left neck garment portions 112, 114 (e.g., such as for use in alternating application of pressure between the right and left sides of the neck).

Further, in one or more embodiments, the neck pressure applying regions 111 may include one or more neck actuatable elements (e.g., non-fluid receiving regions) configured to apply pressure to a portion of the neck (e.g., an electrical signal may be used to actuate an element within the garment, such as electrically actuatable fibers in the garment, such that the compartment including such fibers applies a pressure to a portion of the body). In one or more embodiments, the one or more neck pressure applying regions 111 may include both one or more cells configured to receive fluid and one or more neck actuatable elements.

Any number of pressure applying regions 111 may be configured in the neck garment portion 110 such that they may be controlled to move lymph as described, for example, with reference to FIGS. 2A-2C. For example, as shown in FIG. 4, one pressure applying region 111 is implemented (e.g., although with use of the dotted additional port 119 and the divider 113, two pressure applying regions 111 is also shown as being implemented). The single pressure applying region 111 may extend along the entire length of the neck garment portion 110 positionable about the neck of a user. For example, the pressure applying region 111 may extend within the neck garment portion 110 from a first end 211 to a second end 213. However, such pressure applying regions 111 may include any number of different and separate cells along the wrappable length of the neck garment portion 110 and controllable to produce desired lymph movement (e.g., multiple cells along the length, parallel cells along the width, etc.).

Figure 5:
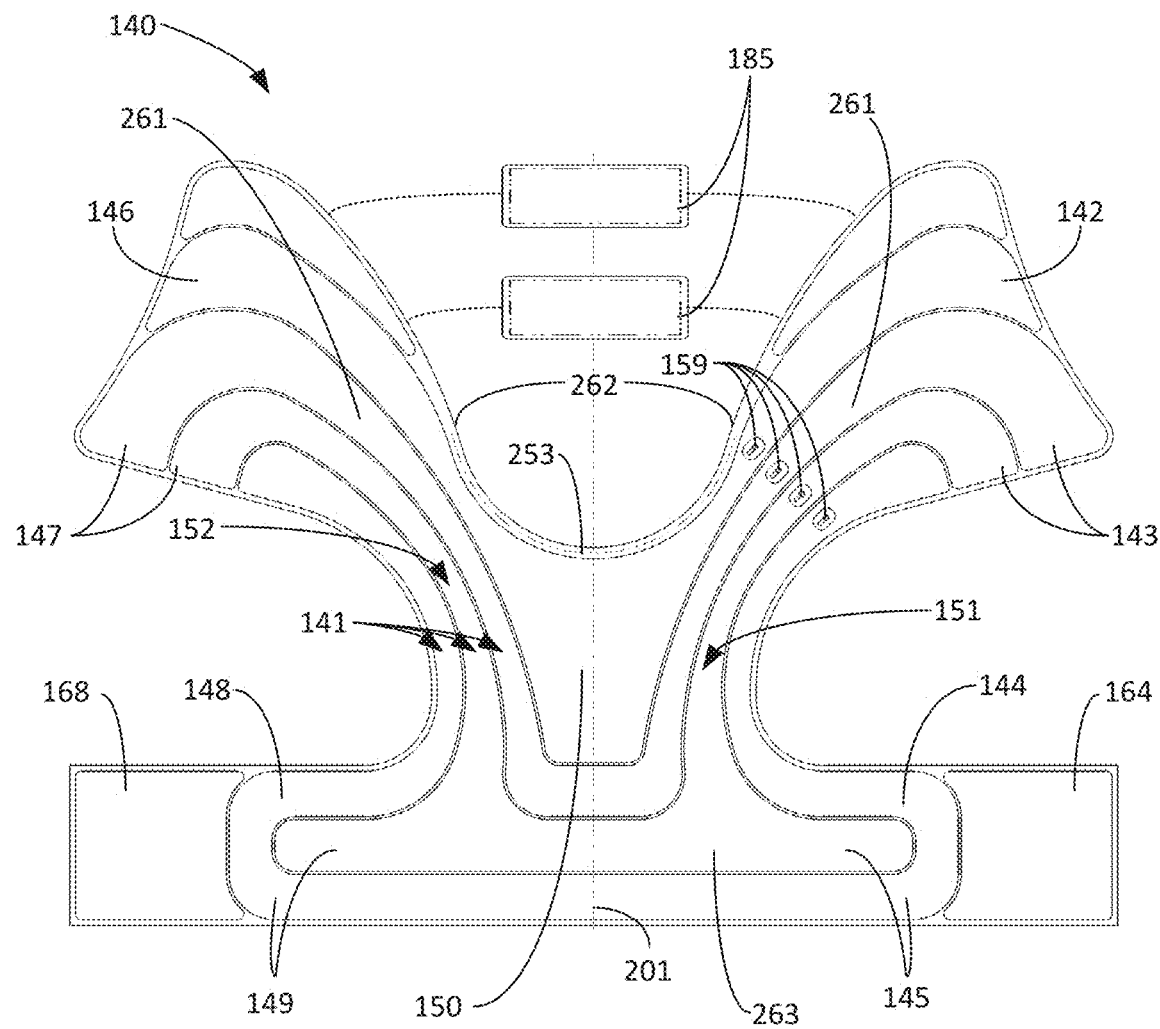
FIG. 5 is a plan view of a torso garment portion of a compression garment system such as shown in FIGS. 1A-1B including one or more pressure applying regions.

A plan view of the exemplary torso garment portion 140 including one or more torso pressure applying regions 141 is shown in FIG. 5. Any number of torso pressure applying regions 141 may be implemented (e.g., the torso garment portion 140 may include eight torso pressure applying regions 141). In one or more embodiments, at least a portion of the one or more torso pressure applying regions 141 may define an arcuate shape (e.g., curved portions of the torso pressure applying regions 141 extending over the shoulders of a user from the posterior to the anterior). For example, arcuate shapes (e.g., of any of the portions of the garment) that may be similar to and include one or more features found in U.S. Pat. No. 6,860,862 entitled "Lymphedema Treatment System," U.S. Pat. No. 6,966,884 entitled "Lymphedema Treatment System," U.S. Pat. No. 6,179,796 entitled "Lymphedema treatment system," and U.S. Pat. No. 6,645,165 entitled "Lymphedema treatment system," which are herein incorporated by reference. The one or more torso pressure applying regions 141 may be configured to be controlled (e.g., using controller 102 as shown in FIGS. 1A-1B) to apply pressure to one or more portions of the torso when the torso garment portion 140 is positioned on the torso.

The one or more torso pressure applying regions 141 may be located in various locations within the torso garment portion 140 to apply pressure to a variety of different locations on the torso. For example, the torso garment portion 140 may include a right torso garment portion 151 positionable proximate the right side of the torso, a left torso garment portion 152 positionable proximate the left side of the torso, and a posterior torso garment portion 150 positionable proximate the posterior of the torso. The one or more torso pressure applying regions 141 associated with the right, left, and posterior torso garment portions 151, 152, 150 may be controllable to apply pressure to the right side, left side, and posterior of the torso, respectively. In one or more embodiments, the right torso garment portion 151 may be described as positioned proximate a right anterior portion and right side of the torso and the left torso garment 152 may be described as positionable proximate a left anterior portion and a left side of the torso; the torso pressure applying regions 141 associated with such regions may be controllable or configured to apply pressure to each of the right and left anterior portions of the torso and the right and left sides of the torso.

In one or more embodiments, each of the one or more torso pressure applying regions 141 may be configured in any suitable manner such that the regions 141 may be controlled to apply pressure to a portion of the torso to move lymph as desired. For example, the one or more torso pressure applying regions 141 may include fluid chambers or cells, pneumatic pressure applying regions, actuatable elements applying pressure to regions, hydraulic pressure applying regions, etc. Specifically, the one or more torso pressure applying regions 141 may include one or more cells configured to receive fluid (e.g., air).

For example, in one or more embodiments, the one or more torso pressure applying regions 141 may be configured to apply pressure to a portion of the torso using the one or more cells through the control of fluid provided thereto, e.g., liquid flow, air flow, etc. For example, the torso garment portion 140 may include one or more torso garment ports 159 through which fluid may be provided to the one or more cells (e.g., such as with use of pump 103 shown in FIG. 1, under control of controller 102 with use of a sensor feedback system).

Further, in one or more embodiments, the one or more torso pressure applying regions 141 may include one or more torso actuatable elements configured to apply pressure to a portion of the torso (e.g., an electrical signal may be used to actuate an element within the garment, such as electrically actuatable fibers in the garment, such that the compartment including such fibers applies a pressure to a portion of the body). In one or more embodiments, the one or more torso pressure applying regions 141 may include both one or more cells configured to receive fluid and one or more torso actuatable elements.

Further, in one or more embodiments, the right torso garment portion 151 may include a right chest garment portion 142 positionable proximate the right shoulder and chest of the torso and a right axillary garment portion 144 positionable proximate the right under arm and right waist of the torso. The right chest garment portion 142 may include one or more right chest pressure applying regions 143 controllable to apply pressure to a portion of the right chest and right shoulder. The right axillary garment portion 144 may include one or more right axillary pressure applying regions 145 controllable to apply pressure to a portion of the torso under the right under arm of the torso.

Still further, the left torso garment portion 152 may also include a left chest garment portion 146 positionable proximate the left shoulder and chest of the torso and a left axillary garment portion 148 positionable proximate the left under arm and left waist of the torso. The left chest garment portion 146 may include one or more left chest pressure applying regions 147 controllable to apply pressure to a portion of the left chest and left shoulder. The left axillary garment portion 148 may include one or more left axillary pressure applying regions 149 controllable to apply pressure to a portion of the torso under the left under arm. Each of the pressure applying regions 141 of the torso garment portion 140 may be controllable to apply pressure to a portion of the torso to move lymph as desired (e.g., downward from the neck and shoulder regions to lower portions of the torso).

Any number of pressure applying regions 141 may be configured in the torso garment portion 140 such that they may be controlled to move lymph as described, for example, with reference to FIGS. 2A-2C. For example, as shown in FIG. 5, a plurality of pressure applying regions 141 are distributed in the torso garment portion 140. In one or more embodiments, the plurality of pressure applying regions 141 may include an upper torso pressure applying region 261 (e.g., adjacent an upper edge 262 of the torso garment portion 140) positionable for applying pressure to the upper posterior torso region and upper anterior torso region of the body. Further, in one or more embodiments, the plurality of pressure applying regions 141 may include a lower torso pressure applying region 263 (e.g., primarily extending in the axillary garment portions 144, 148) positionable for applying pressure primarily to the lower posterior torso region and the lower anterior torso region of the body.

One or more of the pressure applying regions 141 may extend along the entire wrappable length of the torso garment portion 140 (e.g., the wrappable length of the torso garment portion 140 being a length of the curve extending from the left chest garment portion 146 to the right chest garment portion 142). For example, one or more of the pressure applying regions 141 may extend within the left chest garment portion 146, the posterior torso garment portion 150, and the right chest garment portion 142. For example, application of pressure in the upper torso pressure applying region 261 (e.g., next to edge 262), followed by application of pressure by lower pressure applying regions, may produce desired lymph movement. However, such pressure applying regions 141 may include any number of different and separate cells within the torso garment portion 140 and controllable to produce desired lymph movement.

In one or more embodiments (e.g., as shown in FIGS. 1A-1B), the right chest garment portion 142, the right axillary garment portion 144, the left chest garment portion 146, and the left axillary garment portion 148 may be configured to overlap over a portion of the body (e.g., over the anterior portion of the torso of the body). In one or more embodiments, the right chest garment portion 142, the right axillary garment portion 144, the left chest garment portion 146, and the left axillary garment portion 148 may overlap such that the pressure applying regions 143, 145, 147, 149 are positioned next to the portion of the body to which such pressure applying regions are to apply pressure for desired lymph movement. For example, right and left chest garment portions 142, 146 may be positioned on the body first, followed by the right and left axillary garment portions, 144, 148. Furthermore, the right axillary garment portion 144 may define a right axillary garment portion end 164 (e.g., terminating the portion 144) that may be configured to be coupled (e.g., using hook and loop fasteners) to a left axillary garment portion end 168 that is defined by the left axillary garment portion 148 (e.g., terminating the portion 148).

Further, in one or more embodiments, the right and left chest garment portions 142, 146 may be coupled to one another using one or more torso straps 185 (e.g., separate straps connectable, such as with use of hook and loop fasteners, to two different regions 142, 146 of the torso garment portion 140 across the chest of the user when the torso garment portion 140 is being donned). The one or more torso straps 185 may be positioned along the right and left chest garment portions 142, 146 to don the torso garment portion 140 onto the torso of the body. In one or more embodiments, the fastening apparatus 180 (e.g., as shown in FIGS. 1A-1B) may include the one or more torso straps 185.

One will recognize that any number of connection elements may be used to connect regions of the torso garment portion 140 for securing the torso garment portion 140 on the body. Further, one will recognize that the shape and size of the torso garment portion 140 may take one of various forms and is not limited to the wing shaped configuration of FIGS. 3-7. For example, the torso garment portion 140 may take the form of a more vest-like structure with openings to receive a user's arms as described with reference to FIGS. 9-10. Further, for example, the torso garment portion 140 may also include arm garment portions (not shown) which extend along a least a portion of the user's arm from shoulder region of the torso garment.

As shown in FIGS. 3-7, each of the head garment portion 120, the neck garment portion 110, and the torso garment portion 140 is configured in a symmetrical manner generally with reference to the axis of a person's body. In other words, the various garment portions include sub-portions symmetrical about an axis. For example, the head garment portion 120 as shown in FIG. 3 is symmetrical about axis 201 (e.g., one or more sub-portions, such as right cheek garment portion 122 and left cheek garment portion 124 may be symmetrical about axis 201). In one or more embodiments, sub-portions of one or more of the head garment portion 120, the neck garment portion 110, and the torso garment portion 140 which include pressure applying regions may be symmetrical about axis 201, while other portions the head garment portion 120, the neck garment portion 110, or the torso garment portion 140 may be non-symmetrical. Further, in one or more embodiments, non-symmetrical garments are contemplated within the present disclosure (e.g., various garment portions may be non-symmetrical to accomplish one or more various functions such as related to donning or securing the garment on a user).

In one or more embodiments, the one or more pressure applying regions of the head garment portion 120, the neck garment portion 110, and the torso garment portion 140 may be used in conjunction with one another. For example, the one or more neck pressure applying regions 111 may be controllable to apply a pressure to the portion of the neck after the one or more head pressure applying regions 121 are controlled to apply pressure to a portion of the head. In another example, the one or more neck pressure applying regions 111 may be controllable to apply pressure to the portion of the neck and the one or more head pressure applying regions 121 may be controllable to apply pressure to the portion of the head to move lymph from the head towards the neck and downward therefrom. In yet another example, the one or more under chin pressure applying regions 126, the one or more cheek pressure applying regions 123, the one or more posterior head pressure applying regions 129, and the one or more neck pressure applying regions 111 may be configured or controllable to move lymph from a portion under the chin towards the portion of the cheek, from the portion of the cheek towards the portion of the posterior head, and from the portion of the posterior head towards the portion of the neck.

In one or more embodiments, the controller (e.g., controller 102 as shown in FIGS. 1A-1B) may be configured to control pressure applied by each of the one or more head pressure applying regions 121, the one or more neck pressure applying regions 111, and the one or more torso pressure applying regions 141 to move lymph at least from the head to the neck to the torso. In one or more embodiments, each of the head and torso pressure applying regions 121, 141 may be controllable to apply pressure to move lymph at least from the left and right sides of the head towards the posterior of the head and from the posterior of the head downward towards the torso.

Figure 6:
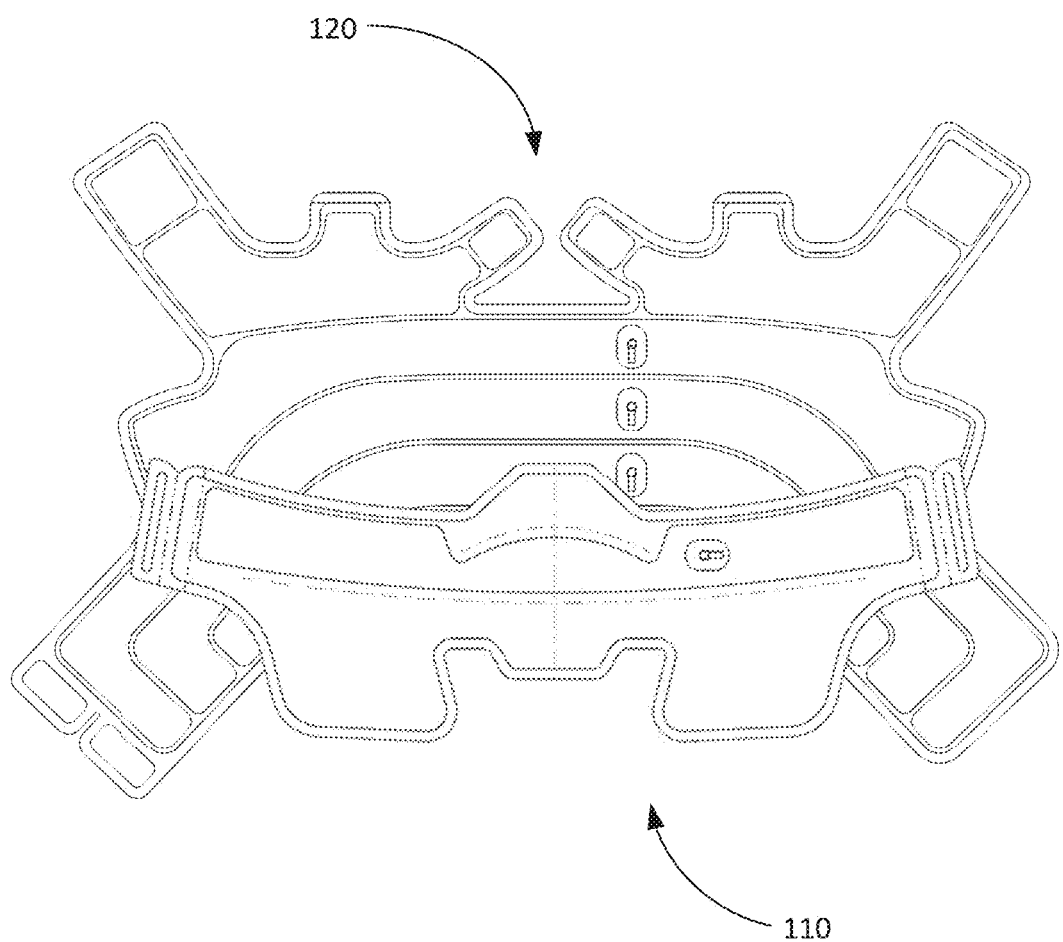
FIG. 6 is a plan view of the exemplary head garment portion of FIG. 3 coupled to the exemplary neck garment portion of FIG. 4.

In one or more embodiments, the head garment portion 120 may be coupled to the neck garment portion 110 as shown in FIG. 6. Any suitable manner may be used to couple the head and neck garment portions 120, 110. For example, such garment portions may be coupled using stitching, welding, or any other coupling technique to form a unitary garment. For example, head garment portion 120 may be attached to neck garment portion 110 at respective seam lines 250, 251. In one or more embodiments, the head garment portion 120 may be attached to the neck garment portion 110 along the entire seam line 250, 251. Further, in one or more embodiments, for example, the head and neck garment portions 120, 110 may be coupled to one another at select locations along the respective seam lines 250, 251 to provide increased flexibility for the head garment portion 120 to move relative to the neck garment portion 110. Specifically, the head and neck garment portions 120, 110 may be coupled such that there are one or more openings between the head and neck garment portions 120, 110 proximate the posterior of the head. In one or more embodiments, the head garment portion 120 may be removably couplable to the neck garment portion 110, for example, using flaps extending outward from one or both of the head garment portion 120 and the neck garment portion 110. In other words, the head garment portion 120 and the neck garment portion 110 may be coupled and uncoupled using any suitable fastener at, e.g., the flaps extending outward from one or both.

Figure 7:
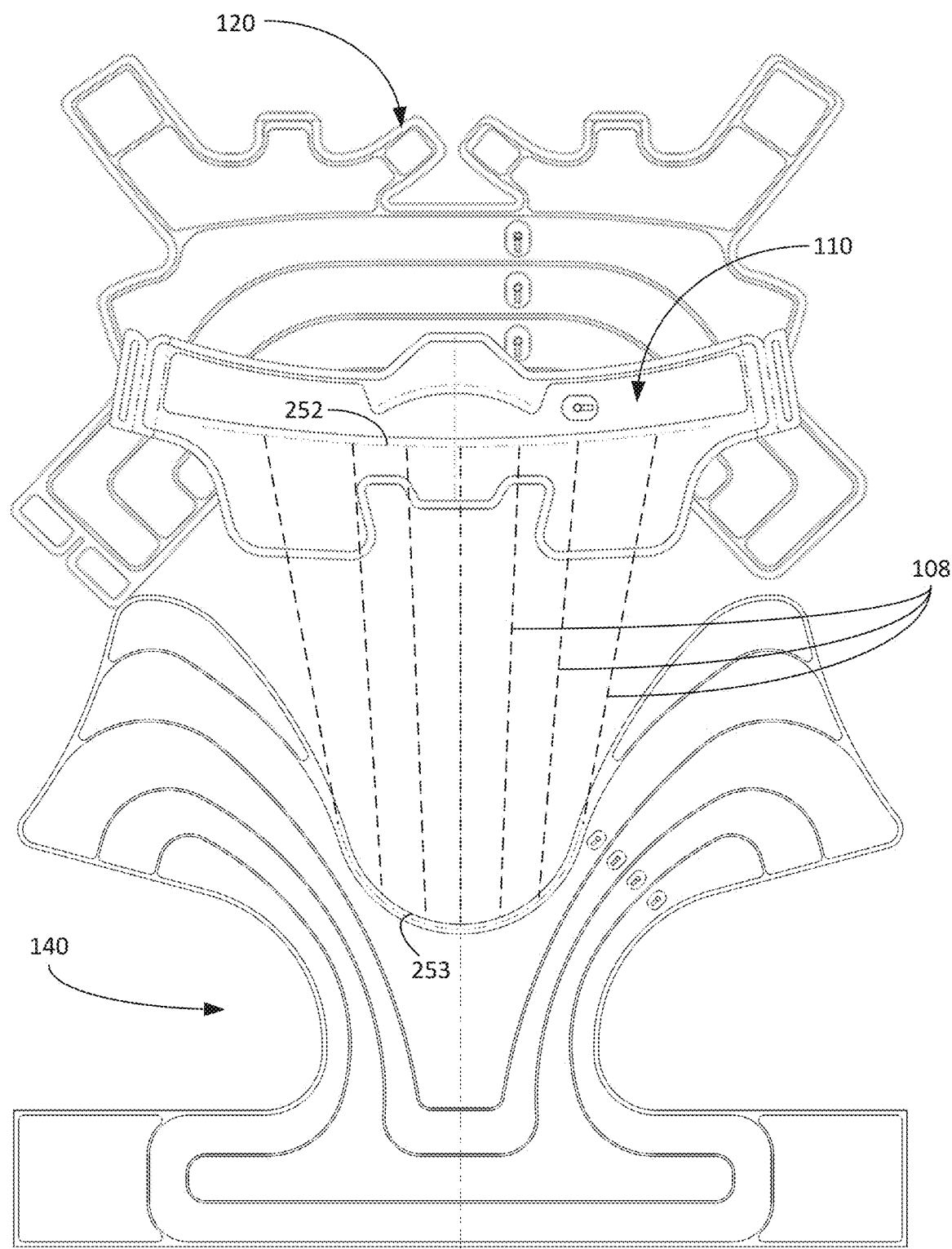
FIG. 7 is a plan view of the exemplary head garment portion of FIG. 3 coupled to the exemplary neck garment portion of FIG. 4 and the exemplary torso garment portion of FIG. 5 couplable to the exemplary neck garment portion of FIG. 4.

In one or more embodiments, the head garment portion 120 and the torso garment portion 140 may be coupled to the neck garment portion 110 as shown in FIG. 7. For example, the head garment portion 120 may be coupled to the neck garment portion 110 as described with reference to FIG. 6. Further, for example, any suitable manner may be used to couple the torso and neck garment portions 140, 110. For example, such garment portions may be coupled using stitching, welding, or any other coupling technique to form a unitary garment. For example, torso garment portion 140 may be attached to neck garment portion 110 at respective seam lines 253, 252. Dashed lines 108 illustrate the points at which the torso garment portion 140 and the neck garment portion 110 may be coupled together along the illustrated seam lines.

In one or more embodiments, the torso garment portion 140 may be attached to the neck garment portion 110 along the entire seam lines 253, 252. Further, in one or more embodiments, for example, the torso and neck garment portions 140, 110 may be coupled to one another at select locations along the respective seam lines 253, 252 to provide increased flexibility for the torso garment portion 140 to move relative to the neck garment portion 110.

Further, in one or more embodiments, the head, neck, and torso garment portions 120, 110, 140 may be coupled to one another in a variety of different ways. For example, the torso garment portion 140 may be coupled to the neck garment portion 110 such that the torso garment portion 140 has increased flexibility to move relative to the neck garment portion 110. For example, the neck and torso garment portions 110, 140 may be coupled to one another such that there are one or more openings between the neck and torso garment portions 110, 140 proximate the posterior of the neck. In one or more embodiments, the torso garment portion 140 may be coupled to the head garment portion 120 (e.g., directly coupled). For example, in one or more embodiments, the head garment portion 120 and the neck garment portion 110 may be provided as a single head/neck garment portion that may be coupled to the torso garment portion 140. In other words, coupling of the head and neck garment portions 120, 110 may include such garment portions being formed as a single unitary garment portion. In one or more embodiments, the torso garment portion 140 may be removably couplable to the neck garment portion 110 and/or the head garment portion 120, for example, using flaps extending outward from one or each of the torso garment portion 140, the head garment portion 120, and the neck garment portion 110. For example, the torso garment portion 140 may have flaps extending from the torso garment portion 140 proximate the neck such that the flaps may have the appearance of a popped up collar. Therefore, the torso garment portion 140 may be coupled and uncoupled to the head garment portion 120 and/or the neck garment portion 110 using any suitable fastener at, e.g., the flaps extending outward from one or both.

A cross-section of a portion 800 of an exemplary garment including one or more cells 803 which may be used in providing any of the garments described herein is shown in FIG. 8A. The garment portion 800 may define an exterior surface 801 and an opposing interior surface 802. The interior surface 802 may be configured to be positioned closer to the human body than the exterior surface 801 when the garment portion 800 is positioned on the body. The one or more cells 803 may be separated in any way that isolates one cell of the one or more cells 803 from another cell of the one or more cells 803. For example, the one or more cells 803 may be separated by welds 805.

The garment portion 800 may include one or more layers 804, with at least one of the one or more layers 804 including a compression layer 806. The compression layer 806 may define a cavity in each of the one or more cells 803 that may be configured to receive a fluid. The compression layer 806 of each of the one or more cells 803 may receive fluid from a source (e.g., from pump 103 shown in FIGS. 1A-1B) to apply pressure to body portion when garment portion 800 is worn by a user. For example, the fluid may be directed to each of the one or more cells 803 in a sequential or in a continuous manner from, e.g., an inlet to the garment portion 800 to an outlet of the garment portion 800, using a single port, etc.

Each of the one or more cells 803 may be (e.g., individually or in groups) filled with fluid to a pressure that is to be applied to the portion of the body by the garment portion 800. Each of the various pressure applying regions described herein may include, e.g., one of the one or more cells 803 or a plurality of the one or more cells 803. In one or more embodiments, different pressure applying regions described herein may include, e.g., the same one or more cells, but may, e.g., be positioned at different locations on the garment.

Figure 8B:
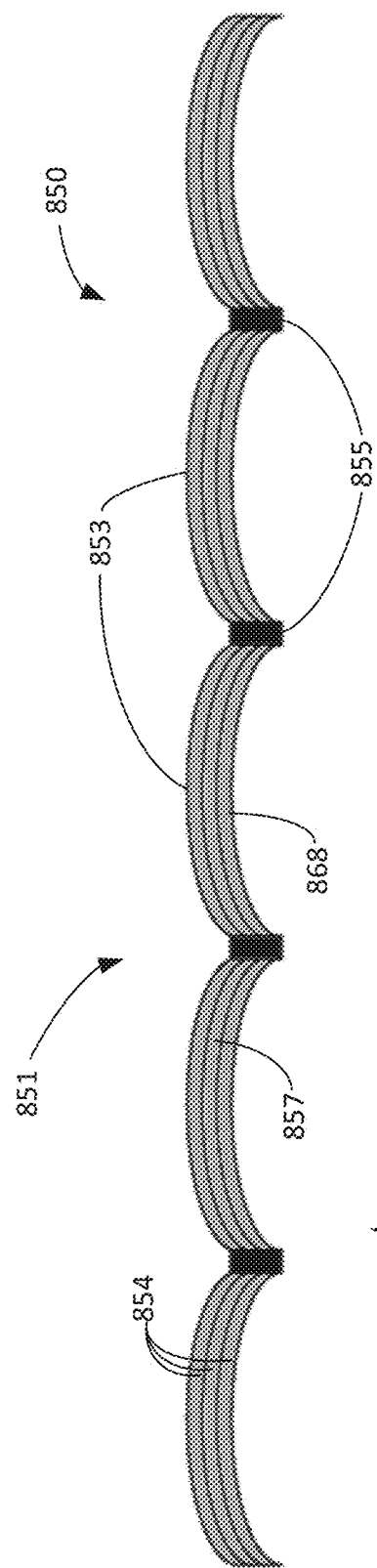
FIG. 8B is a cross-sectional view of one or more cells including actuatable elements (e.g., without inflatable cells) of an exemplary compression garment that may be used with one of the exemplary garment portions such as shown in FIGS. 1A-1B, 3-7, and 9-10.

A cross-section of another portion 850 of exemplary garment including one or more compression regions 853 which may be used in providing any of the garments described herein is shown in FIG. 8B. The garment portion 850 may define an exterior surface 851 and an opposing interior surface 852. The interior surface 852 may be configured to be positioned closer to the human body than the exterior surface 851 when the garment portion 850 is positioned on the body. The one or more regions 853 may be separated or may not need to be separated from one another. In one embodiment, for example, the one or more regions 853 may be separated by welds 855.

The garment 850 may include one or more layers 854, with at least one of the one or more layers 854 including a compression layer 857. The compression layer 857 may include a variety of suitable components configured to apply pressure. For example, the pressure may be applied through the compression layer by an air or pneumatic system, a hydraulic system, an electro-mechanical system, actuated elements (e.g., an electrical signal may be used to actuate an element within the garment, such as electrically actuatable fibers in the garment, such that the compartment including such fibers applies a pressure to a portion of the body), a cable/lace tensioning system, or any other system that is configured to apply pressure to the portion of the body through the garment portion 850.

In at least one embodiment, the compression layer 857 may be a plurality of actuated elements configured to apply pressure to the portion of the body (e.g., actuatable material, such as nitinol, or any other compressing devices). The compression layer 857 of each of the one or more regions 853 may apply pressure to body portion when the garment portion 850 is worn by a user. For example, pressure may be applied by each of the one or more regions 853 in a sequential or in a continuous manner over the one or more regions 853. Each of the various pressure applying regions described herein may include, e.g., one of the one or more regions 853 or a plurality of the one or more regions 853. In one or more embodiments, different pressure applying regions described herein may include, e.g., the same one or more regions, but may, e.g., be positioned at different locations on the garment portion 850.

The garment portions 800, 850, described in FIGS. 8A-8B (and hence as shown in FIGS. 1-7 and 9-10), may also be associated with one or more pressure sensors 818, 868 configured to measure pressure applied to the portion of the body by the garment portions 800, 850. The pressure sensors 818, 868 may be located at a variety of positions along the garment portions 800, 850. For example, the pressure sensors 818, 868 may be positioned (e.g., at an equal distance apart or as necessary) along the length of the garment portions 800, 850. The pressure sensors 818, 868 may be located adjacent the one or more of the pressure applying regions or multiple layers 804, 854 of the garment portions 800, 850.

For example, one layer of material may encompass pressure sensors 818, 868 including pressure sensing regions corresponding to the one or more pressure applying regions and/or corresponding to the one or more cells 803, 853. In one or more embodiments, the pressure sensors 818, 868 may be positioned on a side of the garment portions 800, 850 that may be proximate the portion of the body (e.g., the interior surface 802, 852, etc.). The pressure sensors 818, 868 may be positioned for sensing pressure at, e.g., each pressure applying region, each of the one or more cells 803, 853, a manifold for multiple chambers, etc.

Pressure sensor apparatus may be implemented for sensing pressure in a plurality of different manners at, e.g., each pressure applying region, each air cell or chamber, a manifold for multiple chambers, etc. The pressure sensor apparatus may be configured to measure pressure in a variety of different ways, e.g., one sensor for each pressure applying region, a single sensor for all of the pressure applying regions, etc. Additionally, the controller may be configured to control the pressure applied to the portion of the body based on the measured pressure. For example, pressure sensing apparatus may take the form of using pressure sensor within the garment described in U.S. Pat. No. 9,027,408 entitled "Elastomeric Particle Having An Electrically Conducting Surface, A Pressure Sensor Comprising Said Particles, A Method For Producing Said Sensor And A Sensor System Comprising Said Sensors," or a pump or control apparatus (e.g., 102) may be provided with pressure sensing functionality (e.g., measuring pressures of air in cells as part of the pump apparatus) such as described in U.S. Pat. No. 7,947,003 entitled "Pressurized Medical Device," all of which are incorporated by reference herein.

Figure 9:
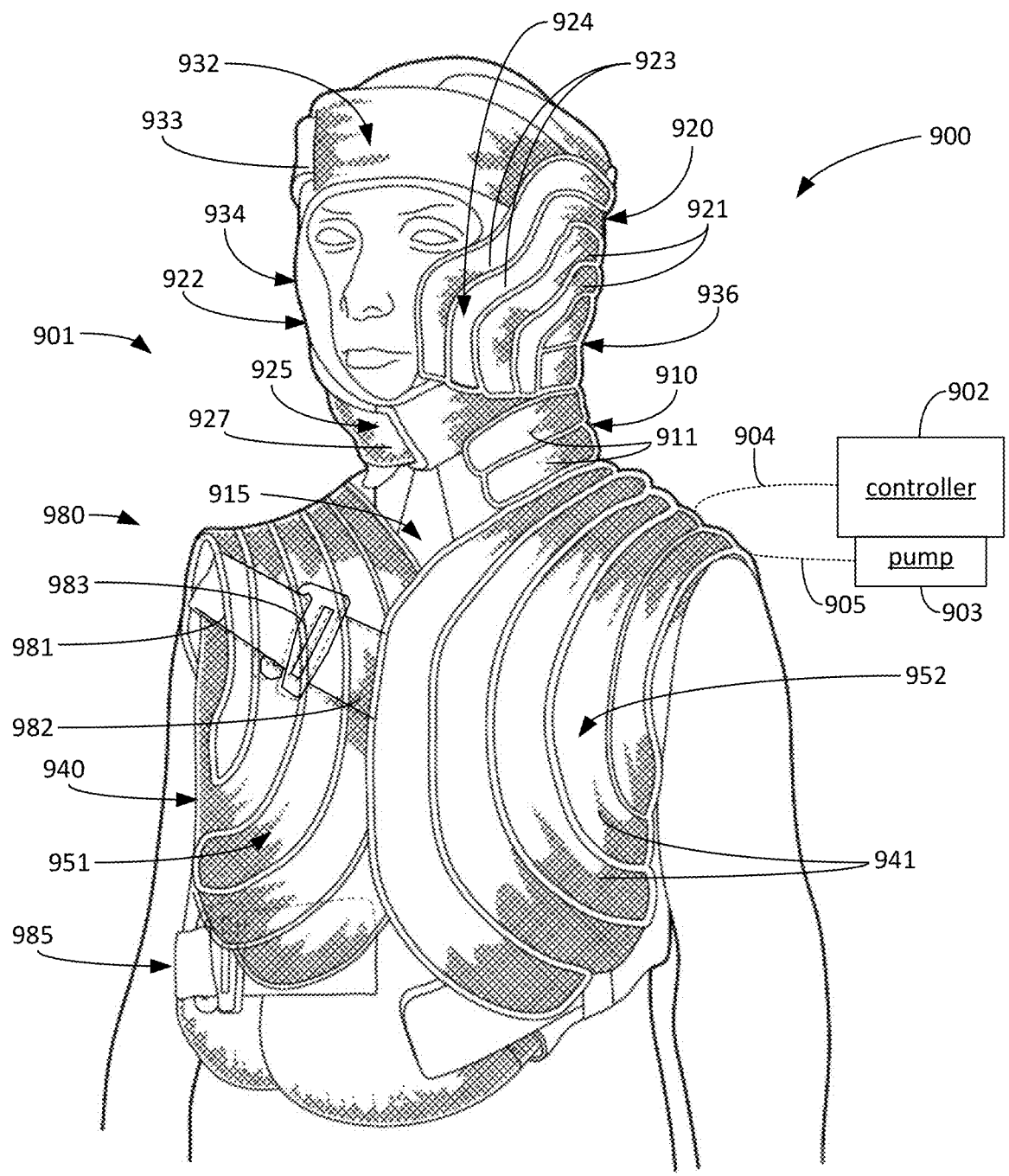
FIG. 9 is a front perspective view of another exemplary compression system located on a body.
Figure 10:
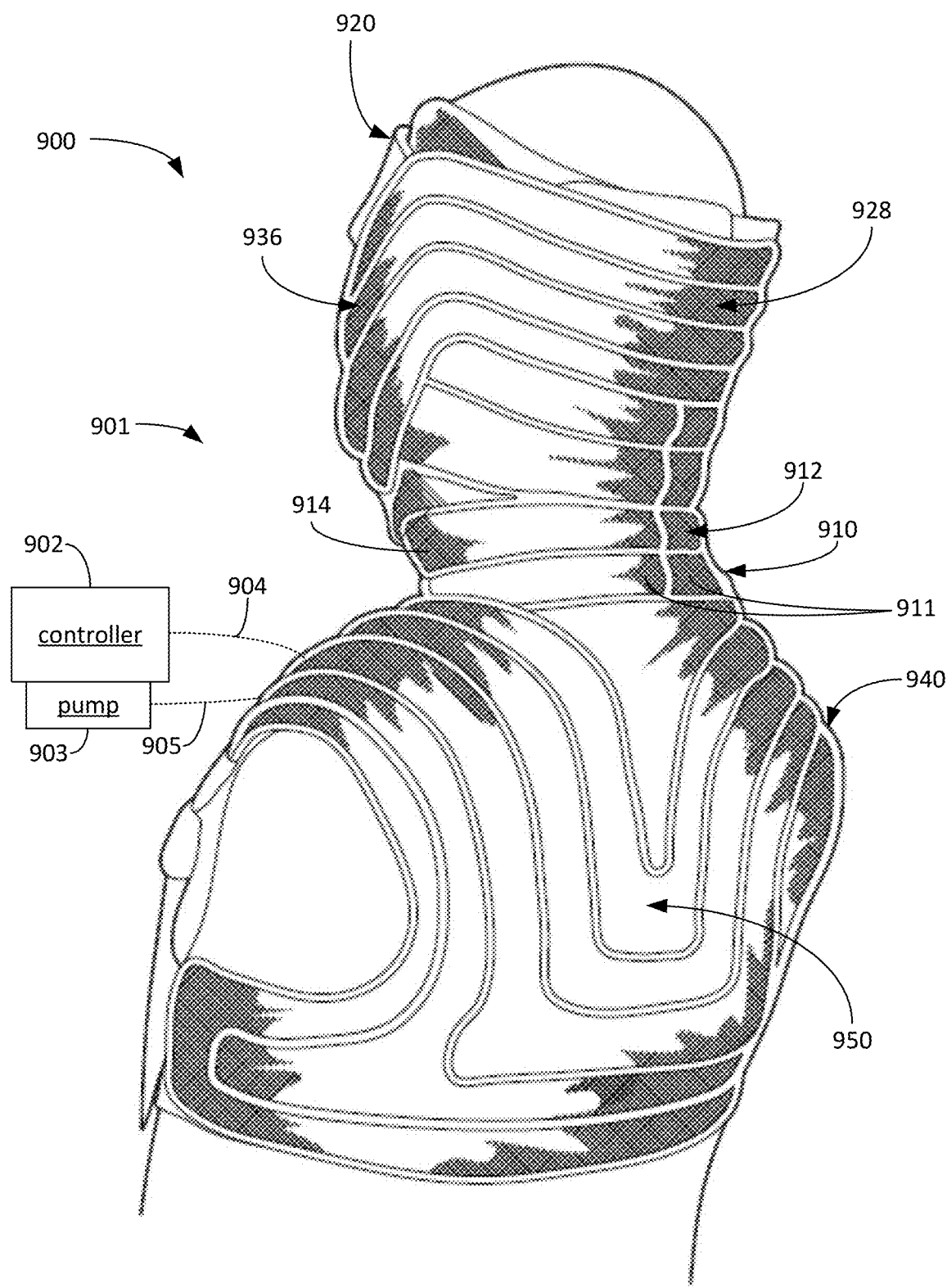
FIG. 10 is a rear perspective view of the exemplary compression system of FIG. 9 located on the body.

Another exemplary compression garment system 900 is illustrated in FIGS. 9-10. The compression garment system 900 may include any of the features shown and/or described herein with reference to FIGS. 1-8, and further, any garments described with reference to FIGS. 1-8 may use any features shown and/or described with reference to FIGS. 9-10. The compression garment system 900 includes a garment 901 configured to be positioned around at least a portion of a body (e.g., a human body 10 as shown in FIGS. 2A-2C). The garment 901 may be positioned relative to the body in a variety of different ways. For example, as shown in FIGS. 9-10, the garment 901 is positioned around the head, neck, and torso of the body.

As shown in FIGS. 9-10, the garment includes a head garment portion 920 positioned proximate the head, a neck garment portion 910 positioned proximate the neck, and a torso garment portion 940 positioned proximate the torso. The head garment portion 920 may be coupled to the neck garment portion 910 and the neck garment portion 910 may be coupled to the torso garment portion 940. In one or more embodiments, the head garment portion 920 may be coupled to the torso garment portion 940. As shown in FIGS. 9-10, the garment 901 may also include an open region 915 between the neck garment portion 910 and the torso garment portion 940 proximate the anterior portion of the neck and adjacent the trachea when the garment 901 is positioned on the body. The open region 915 may allow access to the airway of a patient wearing the garment 901.

The garment 901 may include pressure applying regions located at regions in each portion of the garment 901. Each of the pressure applying regions may be controllable or configured to apply pressure to a portion of the body. For example, the head garment portion 920 may include one or more head pressure applying regions 921 that are controllable or configured to apply pressure to one or more corresponding portions of the head, the neck garment portion 910 may include one or more neck pressure applying regions 911 that are controllable or configured to apply pressure to one or more corresponding portions of the neck, and the torso garment portion 940 may include one or more torso pressure applying regions 941 controllable or configured to apply pressure to one or more corresponding portions of the torso.

The head garment portion 920 may be configured to be donned on the head of the body. In one or more embodiments, the head garment portion 920 may be described as configured to be positioned around both sides of the head from the posterior of the head to the anterior of the head. The head garment portion 920 may include a posterior head garment portion 928, a right head garment portion 934, and a left head garment portion 936. The posterior head garment portion 928 may be positionable proximate a posterior of the head, the right head garment portion 934 may extend from the posterior head garment portion 928 and be positionable on the right side of the head from the posterior of the head to the anterior of the head, and the left head garment portion 936 may extend from the posterior head garment portion 928 and be positionable on the left side of the head from the posterior of the head to the anterior of the head. The head garment portion 920 may also include a right cheek garment portion 922 positionable proximate the right cheek and a left cheek garment portion 924 positionable proximate the left cheek.

The head garment portion 920 may include one or more head pressure applying regions 921. For example, each of the right head garment portion 934, the left head garment portion 936, and the posterior head portion 928 of the head garment portion 920 may include one or more portions of the one or more head pressure applying regions 921. Additionally, the right and left cheek garment portions 922, 924 may include one or more cheek pressure applying regions 923 configured or controllable to apply pressure to a portion of the cheek. The head pressure applying regions 921, and, e.g., the one or more cheek pressure applying regions 923, may work together to help move lymph out of the head and towards the neck and torso.

The head garment portion 920 may also include a forehead garment portion 932 and an under chin garment portion 925. The forehead garment portion 932 and the under chin garment portion 925 may be configured to couple a first portion of the head garment portion 920 to a second portion of the head garment portion 920 to assist in donning and positioning the head garment portion 920 on the head. For example, the under chin garment portion 925 may include one or more under chin connection elements 927 configured to couple the right cheek garment portion 922 to the left cheek garment portion 924. The forehead garment portion 932 and the under chin garment portion 925 may be used to keep portions of the head garment portion 920 (e.g., the right and left cheek garment portions 922, 924) close to the head when the one or more head pressure applying regions 921 are applying pressure to the head. For example, the one or more head pressure applying regions 921 may move the head garment portion 920 away from the body when applying pressure because that direction is the path of least resistance.

The forehead garment portion 932 and the under chin garment portion 925 may be configured to prevent the head garment portion 920 from moving in undesired directions and ensure that the one or more head pressure applying regions 921 are applying pressure to the head when the head garment portion 920 is donned on the head. In one or more embodiments, the head garment portion 920 may include one or more nasal connection elements (not shown) positionable proximate a nasal bridge of the head and configured to connect the first portion of the head garment portion 920 (e.g., the right cheek garment portion 922) to the second portion of the head garment portion 920 (e.g., the left cheek garment portion 924).

In one or more embodiments, the forehead garment portion 932 and the under chin garment portion 925 may be configured to apply pressure to a portion of the head (e.g., the forehead and under the chin, respectively). The forehead garment portion 932 may apply pressure by pulling a strap 933 (e.g., strapping across the upper head garment portion 920) to tighten the forehead garment portion 932 against the forehead. The forehead garment portion 932 may include forehead pressure applying regions (not shown) that are controllable or configured to apply pressure to a portion of the forehead (e.g., temples). Similarly, the under chin garment portion 925 may apply pressure by pulling a strap (e.g., strapping across the lower head garment portion 920) to tighten the under chin garment portion 925 against and under the chin. The under chin garment portion 925 may include under chin pressure applying regions (not shown) that are controllable or configured to apply pressure to a portion under the chin.

As shown in FIGS. 9-10, the neck garment portion 910 may be configured to be donned on a neck of the body. In one or more embodiments, the neck garment portion 910 may be described as configured to be positioned around both sides of the neck from the posterior of the neck to the anterior or sides of the neck. The neck garment portion may include a first neck garment portion 912 (e.g., right neck garment portion) and a second neck garment portion 914 (e.g., left neck garment portion). The first neck garment portion 912 may be positionable proximate a right portion or side of the neck and the second neck garment portion 914 may be positionable proximate a left portion or side of the neck.

Each of the first and second neck garment portions 912, 914 may include one or more neck pressure applying regions 911 controllable or configured to apply pressure to a portion of the neck. For example, the one or more neck pressure applying regions 911 of the first and second neck garment portions 912, 914 may be controllable or configured to apply pressure alternately or simultaneously between each of the first and second neck garment portions 912, 914.

As shown in FIGS. 9-10, the torso garment portion 940 may be configured to be donned on a torso of the body. In one or more embodiments, the torso garment portion 940 may be described as configured to be positioned around both sides of the torso from the posterior of the torso to the anterior of the torso. The torso garment portion 940 may also be described as having a vest-like shape (e.g., a vest including openings at the sides thereof for receiving arms of a user). The torso garment portion 940 may include a posterior torso garment portion 950 positionable proximate the posterior of the torso, a right torso garment 951 positionable proximate the right side of the torso, and a left torso garment 952 positionable proximate the left side of the torso. In one or more embodiments, the right torso garment portion 951 and the left torso garment portion 952 may overlap proximate the anterior of the torso when the garment 901 is positioned on the body.

The torso garment portion 940 may include one or more torso pressure applying regions 941 controllable or configured to apply pressure to a portion of the torso. For example, each of the posterior torso garment portion 950, the right torso garment portion 951, and the left torso garment portion 952 may include one or more torso pressure applying regions 941 controllable or configured to apply pressure to a portion of the posterior of the torso, right side of the torso, and left side of the torso, respectively. Together, the one or more head pressure applying regions 921, the one or more neck pressure applying regions 911, and the one or more torso pressure applying regions 941 may be controllable to apply pressure to portions of the body such that lymph is moved at least from the head towards the torso (e.g., head to torso, head to neck, neck to torso, etc.).

The right and left torso garment portions 951, 952 may be coupled to each other to don the torso garment portion 940 on the torso of the body. The right torso garment portion 951 may be coupled to the left torso garment portion 952 in a variety of different ways. For example, the garment 901 may also include fastening apparatus 980 (e.g., fastening structures) configured to couple the right torso garment portion 951 to the left torso garment portion 952 (e.g., proximate the anterior of the torso). The fastening apparatus 980 may include a right strap 981 couplable to the right torso garment portion 951, a left strap 982 couplable to the left torso garment portion 952, and a fastener 983 configured to couple the right strap 981 to the left strap 982.

The right and left straps 981, 982 may be couplable on the right and left torso garment portions 951, 952, respectively, using hook and loop fasteners. In other words, the right and left straps 981, 982 may be adjustable on the right and left torso garment portions 951, 952 and then coupled together using the fastener 983. This allows the right and left straps 981, 982 to be placed on the torso garment portion 940 in an initial fitting of the torso garment portion 940 on a patient, but then the torso garment portion 940 may be donned and doffed with more ease using the fastener 983. As shown in FIG. 9, the compression garment system 900 includes two fastening apparatus 980, 985, with one on the torso garment portion 940 closer to the neck (e.g., fastening apparatus 980) and another on the torso garment portion 940 closer to the waist (e.g., fastening apparatus 985). The compression garment system may include any number of fastening apparatus 980 suitable for donning the garment 901.

In one or more embodiments, the system 900 may include a control apparatus or controller 902 (e.g., one or more processors employing one or more programs or routines carrying out one or more methods or processes and implemented with one or more types of memory) configured to control the system and/or one or more elements thereof (e.g., providing compression therapy by the one or more pressure applying regions, etc.), and may include a pump 903 and tubing 905 that may be controlled by the controller 902 to provide a fluid to/from the one or more cells (e.g. cells 803 as shown in FIG. 8A) of each of the pressure applying regions, e.g., a fluid such as a liquid or gas in the cells, so as to apply a compression therapy when the garment 901 includes one or more fluid filled cells.

Such control apparatus and pump apparatus may operate in the same manner as described with reference to FIGS. 1A-1B. Further, in one or more embodiments, as shown in FIGS. 9-10, the controller 902 may be connected to one or more components of the compression garment system via one or more electrical lines and/or wirelessly, as represented generally by dashed lines 904. For example, controller 902 may be connected to communicate and control the pressure applying regions either with use of physical electrical connections and/or wirelessly.

The compression garment portions described throughout FIGS. 1-10 may be described as including static garment portions and dynamic garment portions. In other words, static garment portions include portions of the compression garment that may apply a constant pressure (e.g., a static pressure) on a portion of the body during a compression therapy time period and dynamic garment portions include portions of the compression garment that may apply varying pressure on a portion of the body (e.g., under control of a controller) during the compression therapy time period.

In one or more embodiments, a part of the static garment portion may include at least a portion of a dynamic garment portion controlled to apply a static pressure to a portion of the body during the compression therapy time period. For example, a dynamic garment portion may apply a static pressure to a portion of the body by applying a constant pressure to the portion of the body (e.g., strapping a dynamic garment portion tight against the portion of the body to apply a pressure without varying any dynamic pressure applying elements; positioning a dynamic garment portion against the portion of the body and applying a static pressure using the controller (providing fluid to a cell) without varying the pressure being applied). For example, under chin pressure applying elements 126 may be controlled to receive fluid to provide a static pressure under the chin during a compression therapy time period, while other head pressure applying elements may be controlled to apply a dynamic pressure sequence to the head during the compression therapy time period to provide desired lymph movement.

For example, an exemplary garment configured to be donned on a portion of the body (e.g., head, neck, torso, etc.) may include a static garment portion (e.g., under chin garment portion 925) and a dynamic garment portion (e.g., right and left cheek garment portions 922, 924). The static garment portion may be configurable to apply a static pressure to a portion of the head and the dynamic garment portion may include one or more pressure applying regions controllable to apply pressure to a portion of the head and/or neck.

A controller (e.g., controller 102) may be configured to control pressure applied by the one or more pressure applying regions; wherein the pressure may be changed over time during the therapy time period (e.g., dynamic pressure being applied using the one or more pressure applying regions). The one or more pressure applying regions may be controllable to apply pressure to the one or more portions of the head and neck to move lymph at least from the head towards the neck and downward therefrom.

The static garment portion may be configured to apply a static pressure to one or more portions of the body in any suitable manner. For example, the static garment portion may apply pressure during donning of the garment by tightening a portion of the garment in relation to the body. Specifically, for example, the static garment portion may be configurable to apply pressure to a portion under a chin of the head (e.g., through the under chin garment portions 125, 925 illustrated in FIGS. 1A-1B, 3, and 9-10). Static treatment under the chin may help to avoid lymph build-up during compression treatment.

The static garment portion may also include one or more under chin connection elements (e.g., as described in relation to FIGS. 1A-1B) that include a static compression surface positionable proximate under the chin of the head. The one or more under chin connection elements may be configured to connect the right cheek garment portion and the left cheek garment portion. The static garment portion may also be configurable to apply a static pressure to a forehead and temples of the head (e.g., through the forehead garment portions 132, 932 illustrated in FIGS. 1A-1B, 3, and 9-10). Further, for example, the under chin garment portions 125, 925 illustrated in FIGS. 1A-1B, 3, and 9-10, may include under chin pressure applying elements configured to receive fluid to provide a static pressure under the chin during a compression therapy time period (e.g., the one or more under chin cells being filled with fluid and held at a static pressure) while other head pressure applying regions may be controlled to apply a dynamic pressure sequence to the head during the compression therapy time period. However, in one or more embodiments, the one or more pressure applying regions in the under chin garment portions 125, 925 illustrated in FIGS. 1A-1B, 3, and 9-10 may be controllable to apply a dynamic pressure to a portion under the chin.

The dynamic garment portion may be configured to apply dynamic pressure to one or more portions of the body in any suitable manner. For example, the dynamic garment portion may include part of any of the head garment portions, neck garment portions, and/or torso garment portions that include controllable pressure applying regions. The controllable pressure applying regions may work in combination with one another to apply a sequence of pressures on the body that moves lymph in a desired direction (e.g., from the head towards the neck, from the neck towards the torso, etc.). Such application of a sequence of pressures on the body that moves lymph (e.g., pressure, for example, different pressures, being applied to one or more portions of the head and neck, at different times during a compression therapy period) provides a dynamic pressure to the body.

For example, the dynamic garment portion may include a right cheek garment portion (e.g., right cheek garment portion 122, 922) positionable proximate a right cheek of the head and a left cheek garment portion (e.g., left cheek garment portion 124, 924) positionable proximate a left cheek of the head. The one or more pressure applying regions in such right and left cheek garment portions may be controllable to apply a dynamic pressure to a portion of each of the left and right cheeks (e.g., apply a sequence of pressures on the body that moves lymph in a desired direction). In another example, the dynamic garment portion may include a posterior head garment portion (e.g., posterior head garment portion 128, 928) positionable proximate a posterior of the head. The one or more pressure applying regions in the posterior head garment portion may be controllable to apply a dynamic pressure to a portion of the posterior of the head (e.g., apply a sequence of pressures on the body that moves lymph in a desired direction). In other words, any garment portion including pressure applying regions controllable to move lymph suitable to provide a dynamic pressure on the body.

The static and dynamic garment portions may be combined to assist in moving lymph at least from a portion under the chin, a portion of each of the left and right cheeks, and a portion of the posterior of the head towards a portion of the neck. For example, the one or more pressure applying regions may be controllable to apply a dynamic pressure during a therapy time period to move lymph at least from a portion under the chin, a portion of each of the left and right cheeks, and a portion of the posterior of the head towards a portion of the neck, while one or more static garment portions (e.g., such as the under chin garment portions 125, 925 illustrated in FIGS. 1A-1B, 3, and 9-10; or the forehead garment portions 132, 932 illustrated in FIGS. 1A-1B, 3, and 9-10) are used to prevent fluid from movement into the regions upon which the static pressure is being applied during the therapy time period.

Another exemplary compression garment system may include a garment configured to be donned on a head and a neck of a body. The garment may be configurable to apply static pressure to one or more portions of the body (e.g., to under the chin and forehead using a head garment portion) and may include a plurality of pressure applying regions controllable to apply dynamic pressure (e.g., varying pressure over a period of time) to a portion of the body (e.g., to the head, cheeks, posterior of head, neck, torso using a head garment portion, neck garment portion, or torso garment portion).

A controller may be configured to control pressure applied by each of the plurality of pressure applying regions. The pressure may be applied to one or more portions of the head and neck at different times during a compression therapy period. In other words, the garment may apply a static pressure when the garment is donned on a body (e.g., a static pressure is applied by tightening the garment on the body) and then a controller may apply a dynamic pressure to the garment after the garment is donned (e.g., using pressure applying regions to vary pressure at specific regions after the garment is donned on the body). The plurality of pressure applying regions may be controllable to apply pressure to one or more portions of the head and neck to move lymph at least from the head towards the neck and downward therefrom.

The compression garment system may apply pressure to the body through the garment in a variety of different ways. For example, the plurality of pressure applying regions may be controllable to apply dynamic pressure (e.g., varying amounts of pressure applied over therapy period) to one or more portions of the head and neck (e.g., cheeks, neck, and posterior of head using a head garment portion and neck garment portion) after the garment is configured to apply static pressure to one or more portions of the head and neck (e.g., by tightening the garment on the body using, for example, straps, fasteners, etc.). The garment may also be configured to be donned on a torso of the body and the plurality of pressure applying regions may be controllable to apply dynamic pressure to the torso of the body. In one or more embodiments, the garment may also apply a static pressure to the torso when the garment is donned on the torso.

Figure 11:
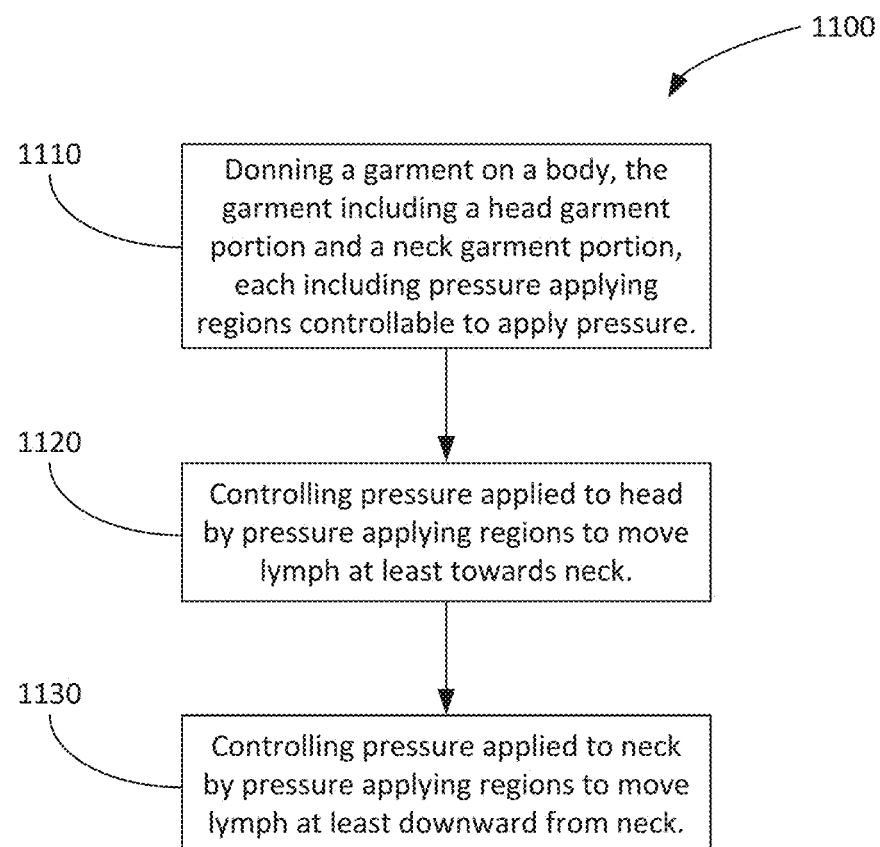
FIG. 11 is a block diagram of an exemplary method of compression therapy that may be implemented using one of the exemplary compression systems of FIGS. 1A-1B and 9-10.

One exemplary method 1100 of compression therapy is illustrated in FIG. 11. The method 1100 may include donning 1110 a garment on at least a portion of a body (e.g., the garment may include a head garment portion and a neck garment portion). The head garment portion may include one or more head pressure applying regions (e.g., controllable to apply pressure to a portion of a head of the body) and the neck garment portion may include one or more neck pressure applying regions (e.g., controllable to apply pressure to a portion of a neck of the body). The method 1100 may also include controlling 1120 pressure applied to the head of the body by each of the one or more head pressure applying regions to move lymph at least towards the neck. The method 1100 may further include controlling 1130 pressure applied to the neck of the body by each of the one or more neck pressure applying regions to move lymph at least downward from the neck.

In one or more embodiments, the method 1100 may also include applying pressure to the head of the body by each of the one or more head pressure applying regions and thereafter applying pressure to the neck of the body by each of the one or more neck pressure applying regions. The method 1100 may further include repeating such application of pressure to the head of the body and to the neck of the body (e.g., a controller controlling the sequence of pressure being applied). In one or more embodiments, the method 1100 may include alternately controlling pressure applied by each of the one or more neck pressure applying regions of a first neck garment portion (e.g., of the neck garment portion and positionable proximate a right portion of the neck) and by each of the one or more neck pressure applying regions of a second neck garment portion (e.g., of the neck garment portion and positionable proximate a left portion of the neck). The first neck garment portion including pressure applying regions separate from those of the second neck garment portion.

In one or more embodiments, the garment may also include a torso garment portion (e.g., positionable proximate a torso of the body) that includes one or more torso pressure applying regions controllable to apply pressure to a portion of the torso. The method 1100 may further include controlling pressure applied to the torso of the body by each of the one or more torso pressure applying regions and repeating application of pressure to the head of the body, to the neck of the body, and to the torso of the body (e.g., a controller controlling the sequence of pressure being applied to each region of the body by the various pressure applying regions of the various garment portions).

Figure 12:
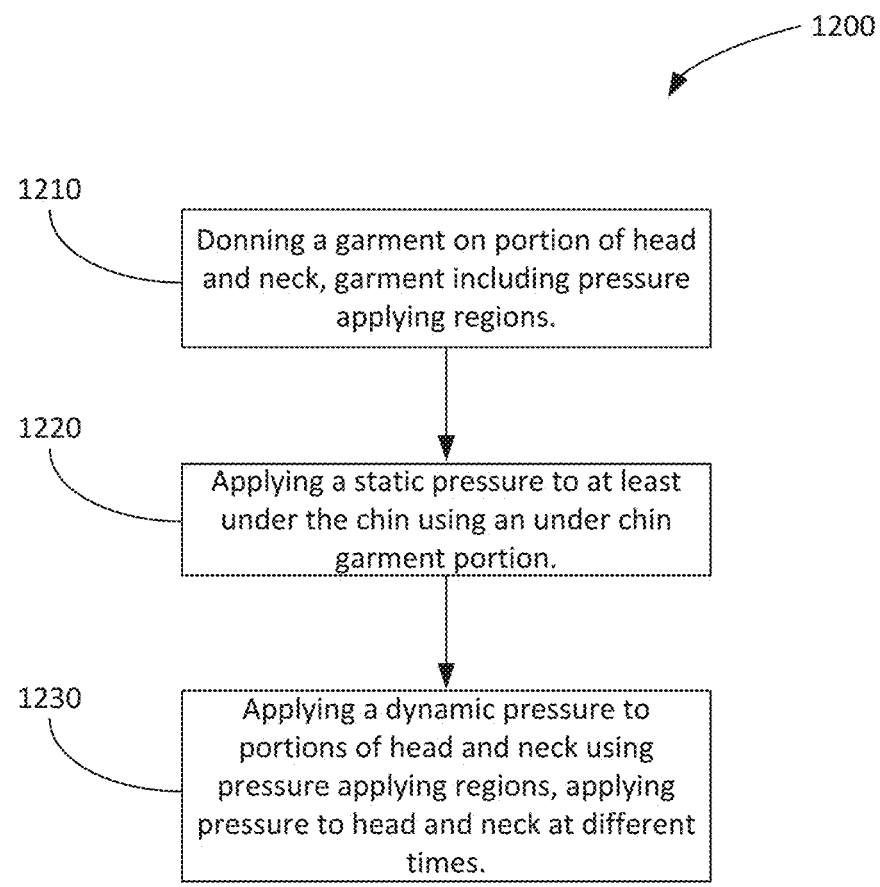
FIG. 12 is a block diagram of another exemplary method of compression therapy that may be implemented using one of the exemplary compression systems of FIGS. 1A-1B and 9-10.

Another exemplary method 1200 of compression therapy is illustrated in FIG. 12. The method 1200 may include donning 1210 a garment (e.g., the garment including a plurality of pressure applying regions) on at least a portion of a head and a neck of a body. The method 1200 may also include applying 1220 a static pressure to at least under a chin of the head using an under chin garment portion of the garment. The method 1200 may further include applying 1230 a dynamic pressure to one or more portions of the head and neck of the body using the plurality of pressure applying regions. The application of a dynamic pressure may include applying pressure to one or more portions of the head and neck at different times during a compression therapy period.

In one or more embodiments, the method 1200 may include controlling the dynamic pressure applied to one or more portions of the head and neck of the body by the plurality of pressure applying regions to move lymph at least from the head and neck downwards. In one or more embodiments, the applying 1230 of a dynamic pressure to the head and neck of the body using the plurality of pressure applying regions may include applying pressure to the head of the body by at least one of the plurality of pressure applying regions and thereafter applying pressure to the neck of the body by at least one of the plurality of pressure applying regions. The applying 1230 of a dynamic pressure may also include repeating application of pressure to the head of the body and to the neck of the body.

In one or more embodiments, the method 1200 may also include donning the garment on at least a portion of a torso of the body (e.g., the garment configured to be donned on at least a portion of the torso of the body may be coupled to the garment configured to be donned on at least a portion of the head and neck of the body) and applying a dynamic pressure to the torso of the body using the plurality of pressure applying regions. In one or more embodiments, the method 1200 may further include applying a static pressure to a forehead and temples of the head using a forehead garment portion of the garment. In one or more embodiments, the method 1200 may also include applying a pressure under the chin of the head using at least one of the plurality of pressure applying regions.

Figure 13A:
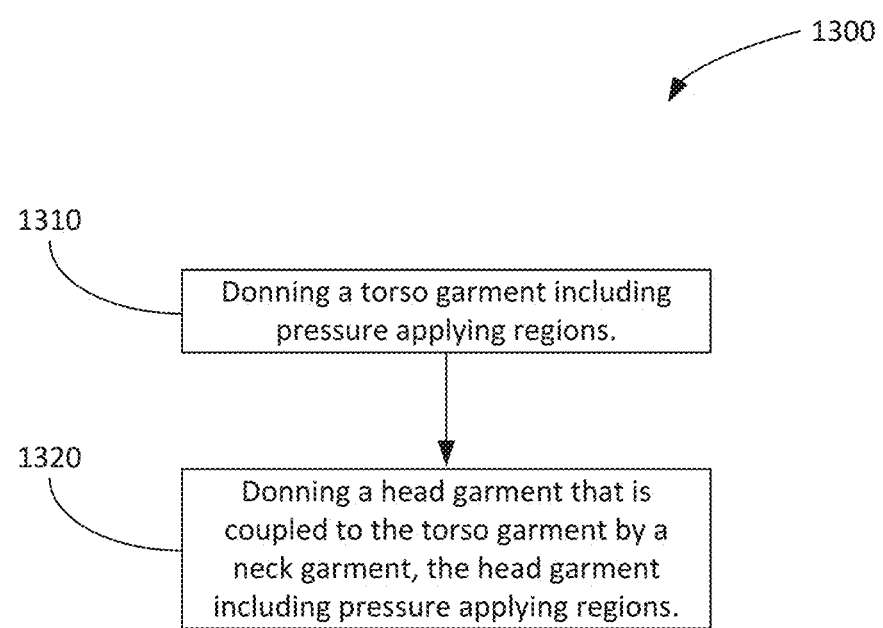
FIG. 13A is a block diagram of yet another exemplary method of compression therapy that may be implemented using one of the exemplary compression systems of FIGS. 1A-1B and 9-10.

Yet another exemplary method 1300 of compression therapy is illustrated in FIG. 13A. The method 1300 may include donning 1310 a torso garment on a torso of the body (e.g., the torso garment may include a plurality of torso pressure applying regions controllable to apply pressure to one or more portions of a torso of the body) and donning 1320 a head garment on the body (e.g., the head garment may be coupled to the torso garment by a neck garment and may include a plurality of head pressure applying regions controllable to apply pressure to one or more portions of a head of the body).

Figure 13B:
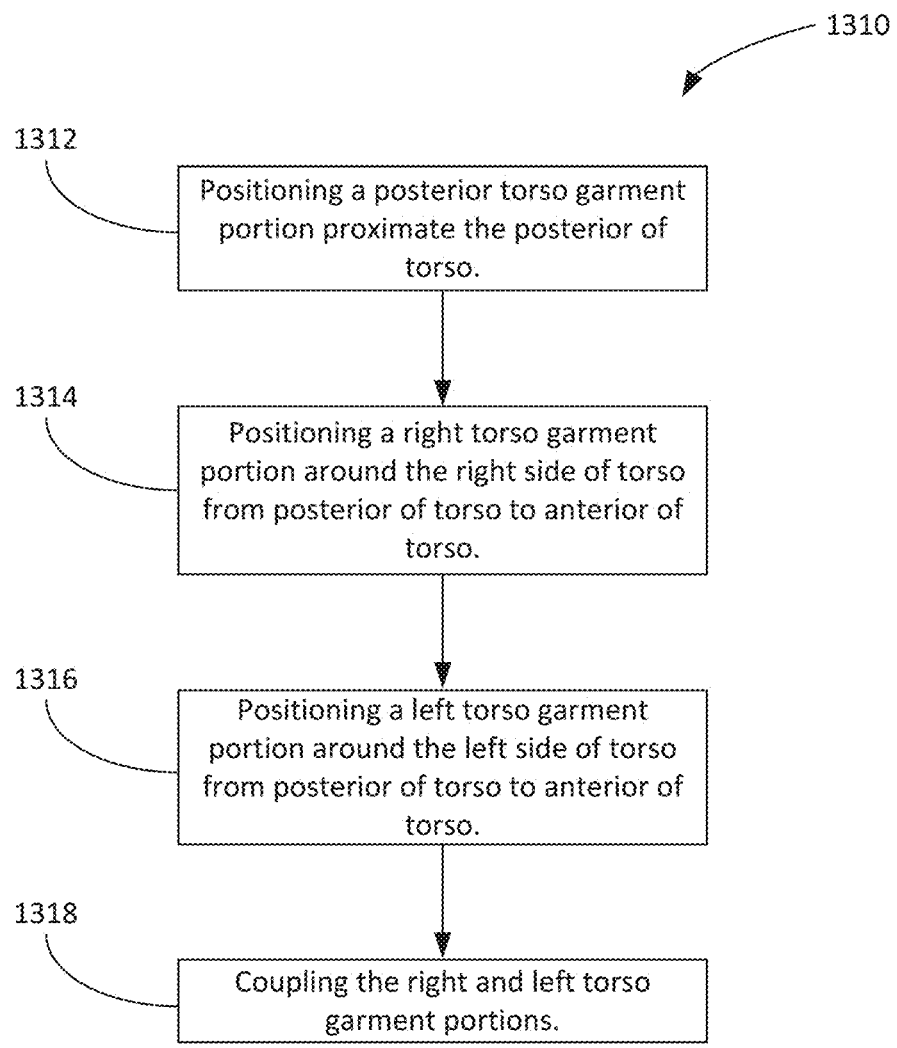
FIG. 13B is a block diagram of one of the processes illustrated by the exemplary method of compression therapy of FIG. 13A.

As shown in FIG. 13B, donning 1310 the torso garment may include positioning 1312 a posterior torso garment portion of the torso garment proximate a posterior of the torso of the body. Donning 1310 the torso garment may also include positioning 1314 a right torso garment portion of the torso garment, extending from the posterior torso garment portion, to an anterior of the torso and positioning 1316 a left torso garment portion of the torso garment, extending from the posterior torso garment portion opposite the right torso garment portion, to the anterior of the torso. Donning 1310 the torso garment may further include coupling 1318 the left and right torso garment portions.

Figure 13C:
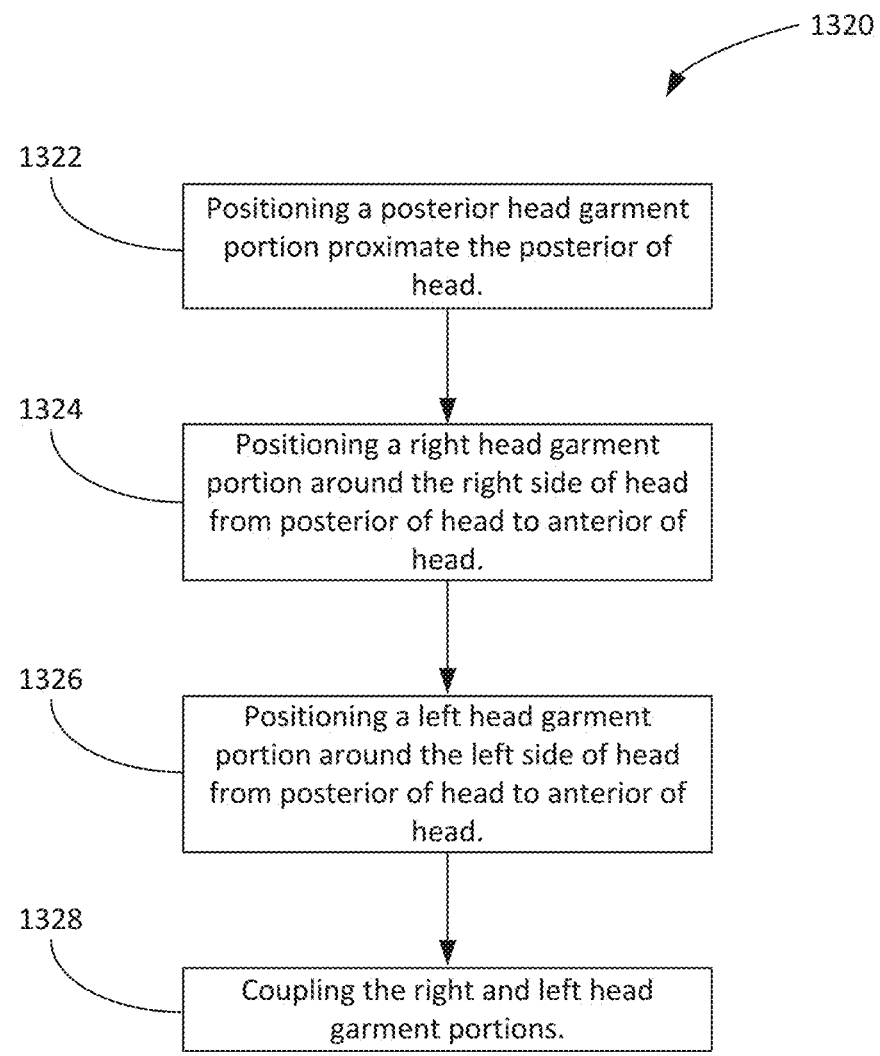
FIG. 13C is a block diagram of another one of the processes illustrated by the exemplary method of compression therapy of FIG. 13A.

Further, as shown in FIG. 13C, donning 1320 the head garment may include positioning 1322 a posterior head garment portion of the head garment proximate a posterior of the head of the body. Donning 1320 the head garment may also include positioning 1324 a right head garment portion of the head garment, extending from the posterior head garment portion, around a right side of the head from the posterior of the head to an anterior of the head and positioning 1326 a left head garment portion of the head garment, extending from the posterior head garment portion opposite the right head garment portion, around a left side of the head from the posterior of the head to the anterior of the head. Donning 1320 the head garment may further include coupling 1328 the right and left head garment portions.

In one or more embodiments, coupling 1318 the left and right torso garment portions may include coupling the left and right torso garment portions using fastening apparatus. In one or more embodiments, the head garment may include a under chin garment portion configurable to apply pressure to a portion under a chin (e.g., the under chin garment portion may be positionable proximate under the chin of the head). The under chin garment portion may include one or more under chin connection elements configured for use in coupling the right and left head garment portions. The head garment may also include a forehead garment portion configured for use in coupling the right and left head garment portions (e.g., the forehead garment portion may be positionable proximate a forehead of the head). The head garment may further include one or more nasal connection elements configured for use in coupling the right and left head garments (e.g., the one or more nasal connection elements positionable proximate a nasal bridge of the head).

In one or more embodiments, each of the plurality of head and torso pressure applying regions may be controllable to apply pressure to a portion of the body to move lymph at least from the left and right sides of the head towards the posterior of the head and from the posterior of the head downward towards the torso. In one or more embodiments, the neck garment includes at least one pressure applying region controllable to apply pressure to a portion of the neck to move lymph from the head downward towards the torso of the body. In one or more embodiments, the method 1300 may include applying pressure to the head of the body by at least one of the plurality of head pressure applying regions and applying pressure to the torso of the body by at least one of the plurality of torso pressure applying regions. In one or more embodiments, the method 1300 may further include repeating application of pressure to the head of the body and to the torso of the body.

Figure 14:
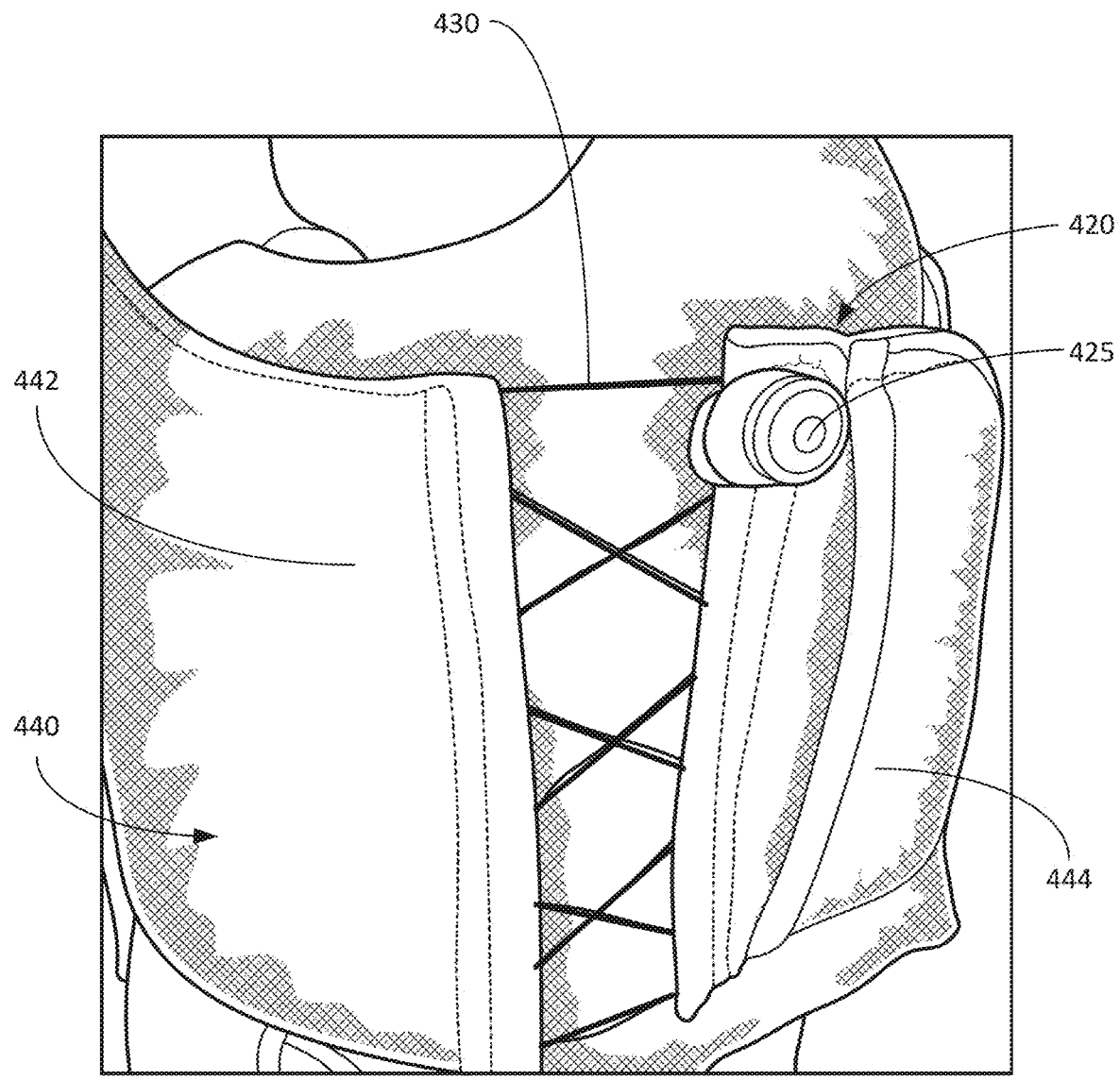
FIG. 14 is on exemplary illustration of a portion of a torso garment including a tightening apparatus (e.g., a lacing system) to assist in donning the garment.

One or more tightening apparatus (e.g., lacing systems) may also be used at one or more locations of the various garments to assist in donning the garment or garments (e.g., on the torso garment along the sides, on the head garment as or with one of the connectors or fasteners, etc.) As shown in FIG. 14, torso garment portion 440 may include a tightening apparatus 420 to assist in positioning (e.g., tightening) the torso garment portion 440 on the torso of the body. The tightening apparatus 420 may be located anywhere on the torso garment portion 440 such that the tightening apparatus 420 helps to move a first portion 442 of the torso garment portion 440 relative to a second portion 444 of the torso garment portion 440 to, e.g., assist in tightening the torso garment portion 440 proximate the torso of the body.

The tightening apparatus 420 may include at least one lace 430 positioned (e.g., laced) between the first and second portions 442, 444 of the torso garment portion 440. The at least one lace 430 may be guided between the first and second portions 442, 444 of the torso garment portion 440 using guide members (e.g., not shown but through which the lace runs, for example, at the ends of the crossing laces). The tightening apparatus 420 may also include a tightening device 425 that may be coupled to the at least one lace 430 and configured to apply tension on the at least one lace 430 to tighten the torso garment portion 440 about the torso of the body.

As shown in FIG. 14 the tightening apparatus 420 is located under an arm of the body. In one or more embodiments, the tightening apparatus 420 may be located under one or both arms of the body (e.g., along the sides of the body). Also, the tightening apparatus 420 may be located in any other location along the garment that may need additional help in tightening or adjusting the garment proximate the body. The tightening apparatus 420 described herein may be similar to and include one or more features found in PCT International Application No. PCT/US2015/036951 entitled "Compression Garment System with Tightening Apparatus," which is herein incorporated by reference.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Particular materials and dimensions thereof recited in the disclosed examples, as well as other conditions and details, should not be construed to unduly limit this disclosure. Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

What is claimed is:

1. A compression garment comprising:
   a head garment configured to be positioned around both sides of a head of a body from a posterior of the head to an anterior of the head, wherein the head garment comprises a plurality of controllable head pressure applying regions positionable proximate at least cheeks and a posterior of the head, each of the plurality of controllable head pressure applying regions comprising one or more cells configured to receive a fluid, wherein the head garment defines an exterior surface and an interior surface opposing the exterior surface, wherein the interior surface is configured to face the body and the exterior surface is configured to face away from the body and be exposed to an external environment, and wherein the head garment further comprises at least one weld formed between the exterior and interior surfaces to define the one or more cells, wherein, during use, one cell of the one or more cells of the head garment extends forward from a posterior portion of the head garment toward a forward portion of the head garment, and further angles downward from the forward portion of the head garment to a cheek portion of the head garment; and a neck garment coupled to the head garment and configured to be positioned around both sides of a neck of the body from a posterior of the neck to an anterior of the neck, wherein the neck garment comprises at least one controllable neck pressure applying regions.

2. The compression garment of claim 1, wherein the compression garment is controllable by a controller configured to control each of the plurality of head controllable pressure applying regions to apply pressure to the cheeks and the posterior of the head and each of the at least one neck controllable pressure applying regions to apply pressure to a portion of the neck to move lymph at least from the cheeks towards the neck and downwards.

3. The compression garment of claim 1, wherein each of the at least one controllable neck pressure applying regions comprises one or more cells configured to receive a fluid.

4. The compression garment of claim 1, wherein each of the plurality of controllable head pressure applying regions comprises one or more head actuatable fibers configured to apply pressure to the cheeks and posterior of the head and each of the at least one controllable neck pressure applying regions comprises one or more neck actuatable fibers configured to apply pressure to the portion of the neck.

5. The compression garment of claim 1, wherein the neck garment defines an open region proximate an anterior portion of the neck of the body adjacent the trachea when positioned on the body.

6. The compression garment of claim 1, wherein the neck garment comprises a right neck garment portion positionable proximate a right portion of the neck of the body and a left neck garment portion positionable proximate a left portion of the neck of the body, wherein at least one controllable neck pressure applying region of the right neck garment portion is separate from at least one controllable neck pressure applying region of the left neck garment portion.

7. The compression garment of claim 6, wherein the compression garment is controllable by a controller configured to control pressure applied by the right and left neck garment portions alternately.

8. The compression garment of claim 1, further comprising a torso garment coupled to the neck garment and configured to be positioned around both sides of a torso of the body from a posterior of the torso to an anterior of the torso, wherein the torso garment comprises a plurality of controllable torso pressure applying regions.

9. A compression garment comprising:
a head garment comprising a plurality of head pressure applying regions controllable to apply pressure to one or more portions of a head of a body, each of the plurality of head pressure applying regions comprising one or more cells configured to receive a fluid, wherein the head garment defines an exterior surface and an interior surface opposing the exterior surface, wherein the interior surface is configured to face the body and the exterior surface is configured to face away from the body and be exposed to an external environment, and wherein the head garment further comprises at least one weld formed between the exterior and interior surfaces to define the one or more cells, wherein the head garment comprises:
  a posterior head garment portion positionable proximate a posterior of the head of the body,
  a right head garment portion extending from the posterior head garment portion and positionable proximate to an anterior of the head,
  a left head garment portion extending from the posterior head garment portion opposite the right head garment portion and positionable proximate to the anterior of the head; and
a cheek garment portion, wherein, during use, one cell of the one or more cells of the head garment extends forward from the posterior head garment portion toward a forward portion of at least one of the right head garment portion and left head garment portion, and further angles downward from the forward portion of at least one of the right head garment portion and left head garment portion to the cheek garment portion of the head garment; and
a torso garment comprising a plurality of torso pressure applying regions controllable to apply pressure to one or more portions of a torso of the body, wherein the torso garment comprises:
  a posterior torso garment portion positionable proximate a posterior of the torso of the body,
  a right torso garment portion extending from the posterior torso garment portion and positionable to an anterior of the torso, and
  a left torso garment portion extending from the posterior torso garment portion opposite the right torso garment portion and positionable to anterior of the torso; and
a neck garment located between at least a portion of the head garment and at least a portion of the torso garment, wherein the plurality of head and torso pressure applying regions are controllable to move lymph from the head downward to the torso of the body.

10. The compression garment of claim 9, wherein the neck garment comprises at least one pressure applying region controllable to apply pressure to a portion of the neck to at least move lymph from the head downward towards the torso of the body, and further wherein the neck garment is coupled to at least the head garment.

11. The compression garment of claim 10, wherein each of the plurality of head and torso pressure applying regions is controllable to apply pressure to move lymph at least from the left and right sides of the head towards the posterior of the head and from the posterior of the head downward towards the torso.

12. The compression garment of claim 10, wherein the right torso garment portion is positionable proximate a right anterior portion and a right side of the torso and the left torso garment portion is positionable proximate a left anterior portion and a left side of the torso, wherein at least one of the plurality of torso pressure applying regions is controllable to apply pressure to each of the right and left anterior portions of the torso and the right and left sides of the torso.

13. The compression garment of claim 10, wherein the right torso garment portion defines a right arm opening proximate a right arm of the body and the left torso garment portion defines a left arm opening proximate a left arm of the body.

14. The compression garment of claim 10, wherein the right torso garment portion and the left torso garment portion overlap proximate the anterior of the torso when positioned on the body.

15. The compression garment of claim 10, wherein the neck garment comprises a right neck garment portion positionable around a right side of the neck from a posterior of the neck to an anterior of the neck and a left neck garment portion positionable around a left side of the neck from a posterior of the neck to an anterior of the neck, wherein the right neck garment portion comprises pressure applying regions separate from pressure applying regions of the left neck garment portion.

16. The compression garment of claim 10, wherein the torso garment further comprises fastening apparatus configured to couple the right torso garment portion to the left torso garment portion proximate the anterior of the torso, wherein the fastening apparatus comprises at least one strap couplable between the right torso garment portion and the left torso garment portion.

17. The compression garment of claim 16, wherein the at least one strap comprises a right strap couplable to the right torso garment portion and a left strap couplable to the left torso garment portion, and wherein the fastening apparatus further comprises a fastener configured to couple the right strap to the left strap, wherein the left and right straps are couplable on the left and right torso garment portions, respectively, using hook and loop fasteners.

18. The compression garment of claim 10, wherein each of the plurality of torso pressure applying regions comprises one or more cells configured to receive a fluid.

19. The compression garment of claim 10, wherein each of the plurality of head pressure applying regions comprises one or more actuatable fibers configured to apply pressure to the one or more portions of the head and each of the plurality of torso pressure applying regions comprises one or more actuatable fibers configured to apply pressure to the one or more portions of the torso.

20. The compression garment of claim 10, wherein the head garment defines one or more head open regions proximate a top portion of the head.

21. The compression garment of claim 10, wherein the right head garment portion is positionable proximate a right cheek of the head of the body and the left head garment is positionable proximate a left cheek of the head of the body, wherein the plurality of head pressure applying regions are controllable to apply pressure to a portion of right and left cheeks.

22. The compression garment of claim 10, wherein the head garment comprises an under chin garment portion positionable proximate under a chin of the head, wherein the plurality of head pressure applying regions comprises one or more under chin pressure applying regions at the under chin garment portion, the one or more under chin pressure applying regions controllable to apply pressure to a portion under the chin.

23. The compression garment of claim 22, wherein the under chin garment portion comprises one or more under chin connection straps configured for use in donning the head garment on the head of the body, wherein the one or more under chin connection straps are configured to connect the right head garment portion and the left head garment portion.

24. The compression garment of claim 10, wherein the head garment comprises a forehead garment portion positionable proximate a forehead of the head, wherein the forehead garment portion comprises one or more forehead connection straps configured for use in donning the head garment on the head.

25. The compression garment of claim 24, wherein the forehead garment portion is configurable to apply pressure to a portion of the forehead.

26. The compression garment of claim 10, wherein the head garment comprises one or more nasal connection straps positionable proximate a nasal bridge of the head, wherein the one or more nasal connection straps are configured to connect the right head garment portion and the left head garment portion.

27. The compression garment of claim 10, wherein the torso garment portion comprises a tightening apparatus configured to tighten the torso garment portion proximate the body, wherein the tightening apparatus comprises:
at least one lace positioned between a first and second portion of the torso garment portion; and
a tightening device coupled to the at least one lace and configured to apply tension on the at least one lace to move the first portion of the torso garment portion relative to the second portion of the torso garment portion.

28. A method of donning a compression garment on at least a portion of a body, the method comprising:
donning a torso garment on a torso of the body, wherein the torso garment comprises a plurality of torso pressure applying regions controllable to apply pressure to one or more portions of a torso of the body, wherein donning the torso garment comprises:
positioning a posterior torso garment portion of the torso garment proximate a posterior of the torso of the body,
positioning a right torso garment portion of the torso garment, extending from the posterior torso garment portion to an anterior of the torso,
positioning a left torso garment portion of the torso garment, extending from the posterior torso garment portion opposite the right torso garment portion to the anterior of the torso,
coupling the left and right torso garment portions; and
donning a head garment on the body, wherein the head garment comprises a plurality of head pressure applying regions controllable to apply pressure to one or more portions of a head of the body, each of the plurality of head pressure applying regions comprising one or more cells configured to receive a fluid, wherein the head garment defines an exterior surface and an interior surface opposing the exterior surface, and wherein the head garment further comprises at least one weld between the exterior and interior surfaces to define the one or more cells, wherein donning the head garment comprises:
positioning a posterior head garment portion of the head garment proximate a posterior of the head of the body,
positioning a right head garment portion of the head garment, extending from the posterior head garment portion, around a right side of the head from the posterior of the head to an anterior of the head, positioning a left head garment portion of the head garment, extending from the posterior head garment portion opposite the right head garment portion, around a left side of the head from the posterior of the head to the anterior of the head;

positioning a cheek garment portion of the head garment proximate a cheek of the head of the body, wherein one cell of the one or more cells of the head garment extends forward from the posterior head garment portion toward a forward portion of at least one of the right head garment portion and left head garment portion, and further angles downward from the forward portion of at least one of the right head garment portion and left head garment portion to the cheek garment portion of the head garment; and adjustably coupling the right and left head garment portions using a forehead garment portion of the head garment portion positionable proximate a forehead of the body between the right and left head garment portions.

* * * * *